United States Patent [19]

Sloma et al.

[11] Patent Number: 5,589,383
[45] Date of Patent: Dec. 31, 1996

[54] PROTEASE DELETION

[75] Inventors: Alan Sloma, Watertown; Gerald A. Rufo, Jr., Burlington; Cathy F. Rudolph, Stoughton; Barbara J. Sullivan, Burlington; Janice Pero, Lexington, all of Mass.

[73] Assignee: Omnigene, Inc., Cambridge, Mass.

[21] Appl. No.: 285,477

[22] Filed: Aug. 12, 1994

Related U.S. Application Data

[60] Division of Ser. No. 579,401, Sep. 7, 1990, which is a continuation-in-part of Ser. No. 396,521, Aug. 21, 1989, abandoned, which is a continuation-in-part of Ser. No. 347,428, May 4, 1989, abandoned, which is a continuation-in-part of Ser. No. 273,423, Nov. 18, 1988, abandoned.

[51] Int. Cl.$^6$ .............................. C12N 1/21; C12N 9/54; C12N 15/57; C12N 15/75
[52] U.S. Cl. ................. 435/252.31; 435/221; 435/320.1; 536/23.2
[58] Field of Search ................................ 435/221, 252.3, 435/320.1, 252.31; 536/23.2; 424/94.64

[56] References Cited

U.S. PATENT DOCUMENTS 4,828,994   5/1989   Fahnestock et al. .................. 435/172.3

FOREIGN PATENT DOCUMENTS

WO86/01825   3/1986   WIPO.

OTHER PUBLICATIONS

Band et al., Construction and Properties of an Intracellular Serine Protease Mutant of *Bacillus subtilis*, Journal of Bacteriology 169:444–446, 1987.
Beall et al., Cloning and Characterization of *Bacillus subtilis* Homologs of *Escherichia coli* Cell Division Genes ftsZ and ftsA, Journal of Bacteriology 170:4855–4864, 1988.
Bruckner and Doi, Characterization of a Gene for a Minor Extracellular Protease from *Bacillus subtilis*, Abstract, No. 13, Fourth Conference on Genetics and Biotechnology of Bacilli, San Diego, CA, 1987.
Bruckner et al., Characterization of a Gene for a Minor Extracellular Protease of *Bacillus subtilis* Produced During Sporulation, Abstract, No. 49, Program of the Tenth Int'l Spores Conference, Woods Hole, MA, 1988.
Fahnestock and Fisher, Protease-Deficient *Bacillus subtilis* Host Strains for Production of Staphylococcal Protein A, Applied and Environmental Microbiology 53:379–384, 1987.
Ferrari et al., Effect of Stage O Sporulation Mutations on Subtilisin Expression, Journal of Bacteriology, 166:173:173–179, 1986.
Kawamura and Doi, Construction of a *Bacillus subtilis* Double Mutant Deficient in Extracellular Alkaline and Neutral Proteases, J. Bacteriol. 160:442–444, 1984.
Koide et al., Cloning and Sequencing of the Major Intracellular Serine Protease Gene of *Bacillus subtilis*, J. Bacteriol. 167:110–116, 1986.

Ohmura et al., A *Bacillus subtilis* Secretion Vector System Derived from the *B. subtilis* A–Amylase Promoter and Signal Sequence Region, and Secretion, J. Biochem. 95:87–93, 1984.
Palva et al., Secretion of Interferon by *Bacillus subtilis*, Gene 22:229–235, 1983.
Roitsch and Hageman, Bacillopeptidase F: Two Forms of A Glycoprotein Serine Protease From *Bacillus subtilis* J. of Bacteriology 155:152, 1983.
Sloma et al., Gene Encoding a Minor Extracellular Protease in *Bacillus subtilis*, J. of Bacteriology 170–5557–5563, 1988.
Sloma et al., Bacillopeptidase F of *Bacillus subtilis*: Purification of the Protein and Cloning of the Gene J. of Bacteriology 172:1470–1477, 1990.
Smith et al., Characterization of Signal–Sequence–Coding Regions Selected From the *Bacillus subtilis* Chromosome, Gene 70:351–361, 1988.
Srivastava and Aronson, Isolation and Characterization of a Unique Protease from Sporulating Cells of *Bacillus subtilis*, Arch Microbiol 129:227–232, 1981.
Stahl and Ferrari, Replacement of the *Bacillus subtilis* Subtilisin Structural Gene with an In Vitro–Derived Deletion Mutation, J. of Bacteriology 158:411–418, 1984.
Yang et al., Cloning of the Neutral Protease Gene of *Bacillus subtilis* and the Use of the Cloned Gene to Create an In Vitro–Derived Deletion Mutation, J. of Bacteriology, 160:15–21, 1984.
Brückner et al., Multiple Active Forms of a Novel Serine Protease From *Bacillus subtilis*, Mol. Gen Genet 221:486–490, 1990.
Rufo et al., Isolation and Characterization of a Novel Extracellular Metalloprotease From *Bacillus subtilis*, Journal of Bacteriology 172:1019–1023, 1990.
Sloma et al., Bacillopeptidase F of *Bacillus subtilis*: Purification of the Protein and Cloning of the Gene, Errata, J. Bact. 172:5520–5521, Sep. 1990.
Sloma et al., Gene Encoding a Novel Extracellular Metalloprotease in *Bacillus subtilis*, J. of Bacteriology 172:1024–1029, 1990.
Wang et al., Construction of *Bacillus subtilis* Mutant–Deficient in Three Extracellular Proteases, J. Gen. Appl. Microbiol. 35:487–492, 1989.
Wu et al., Cloning Genetic Organization, and Characterization of a Structural Gene Encoding Bacillopeptidase F From *Bacillus subtilis*, The Journal of Biological Chemistry 265:6845–6850, 1990.

Primary Examiner—Dian C. Jacobson
Attorney, Agent, or Firm—Fish & Richardson P.C.

[57] ABSTRACT

A Bacillus cell contains a mutation in the epr gene resulting in inhibition of the production by the cell of the proteolytically active epr gene product; the cell may further contain mutations in the genes encoding proteolytically active residual protease I (bpr) and proteolytically active residual protease II (RP-II).

3 Claims, 33 Drawing Sheets

-446 ATCCGAGCTTATCGGCCCACTCGTCGTTCCCAAACACACTCGCCATGAAATCAGCATACCCC
GGAATCGGGCAAGCTCGTTAAATCAAGAAGACAGACCGATAATAATCAGCGGCATGGT
CAGGATAATCCGTCACGCAAAGCGCTGAGATGCCGCTGCCCCGGCAATTTCCCGGCGAC
AGGCATTATTTTTCCTCATCACCCGAGTGAATGTGCTCATCTTAAAAACCCCCTTTT
CTCATTGCTTTGTGAACAACCTCCCTCTTTCTTTATCTTTATTTTGAAACGCTTA
CAAATTCATTGGAAAAATTTCATGCGAAAAATCTGCATTTGCTAAACAAC
CCTGCCCATGAAATCATAGAAAATCATAGAAAAAGGAGATGAATC
TATATCAAACATCATAGAAAAAGGAGATGAATC

+1  ATG AAA AAC ATG TCT TGC AAA CTT GTT GTA TCA GTC ACT CTG TTT
    met lys asn met ser cys lys leu val val ser val thr leu phe 46  TTC AGT TTT CTC ACC ATA GGC CCT CTC GCT CAT GCG CAA AAC AGC
    phe ser phe leu thr ile gly pro leu ala his ala gln asn ser 91  AGC GAG AAA GAG GTT ATT GTG GTT TAT AAA AAC AAG GCC GGA AAG
    ser glu lys glu val ile val val tyr lys asn lys ala gly lys 136 GAA ACC ATC CTG GAC AGT GAT GCT GAT GTT GAA CAG CAG TAT AAG
    glu thr ile leu asp ser asp ala asp val glu gln gln tyr lys

FIG. 6-1

```
181  CAT CTT CCC GCG GTA GCG CTG ACA GCA GAC CAG GAG ACA GTA AAA
     his leu pro ala val ala val thr ala asp gln glu thr val lys
                             BamHI
226  GAA TTA AAG CAG GAT CCT GAT ATT TTG TAT GTA GAA AAC AAC GTA
     glu leu lys gln asp pro asp ile leu tyr val glu asn asn val
271  TCA TTT ACC GCA GAC AGC ACG GAT TTC AAA GTG CTG TCA GAC
     ser phe thr ala ala asp ser thr asp phe lys val leu ser asp
316  GGC ACT GAC TCT GAC AAC TTT GAG CAA TGG AAC CTT GAG CCC
     gly thr asp ser asp asn phe glu gln trp asn leu glu pro
361  ATT CAG GTG AAA CAG GCT TGG AAG GCA CTG ACA GGA AAA AAT
     ile gln val lys gln ala trp lys ala leu thr gly lys asn
406  ATC AAA ATT GCC GTC ATT GAC AGC ATC TCC CCC CAC GAT GAC
     ile lys ile ala val ile asp ser ile ser pro his asp asp
451  CTG TCG ATT GCC GGG TAT TCA GCT GTC AGT TAT ACC TCT TCT
     leu ser ile ala gly tyr ser ala val ser tyr thr ser ser
```

FIG. 6-2

```
496  TAC AAA GAT GAT AAC GGC CAC GGA ACA CAT GTC GCA GGG ATT ATC
     tyr lys asp asp asn gly his gly thr his val ala gly ile ile 541  GGA GCC AAG CAT AAC GGC TAC GGA ATT GAC GGC ATC GCA CCG GAA
     gly ala lys his asn gly tyr gly ile asp gly ile ala pro glu 586  GCA CAA ATA TAC GCG GTT AAA GCG CTT GAT CAG AAC GGC TCT GGG
     ala gln ile tyr ala val lys ala leu asp gln asn gly ser gly 631  GAT CTT CAA AGT CTT CTC CAA GGA ATT GAC TGG TCG ATC GCA AAC
     asp leu gln ser leu leu gln gly ile asp trp ser ile ala asn 676  AGG ATG GAC ATC GTC AAT ATG AGC CTT GGC ACG ACG TCA GAC AGC
     arg met asp ile val asn met ser leu gly thr thr ser asp ser 721  AAA ATC CTT CAT GAC GCC GTG AAC GCA TAT GAA CAA GGT GTT
     lys ile leu his asp ala val asn lys ala tyr glu gln gly val 766  CTG CTT GTT GCC GCA AGC GGT AAC GAC GGA AAC GGC AAG CCA GTG
     leu leu val ala ala ser gly asn asp gly asn gly lys pro val
```

FIG. 6-3

```
811  AAT TAT CCG GCG GCA TAC AGC AGT GTC GTT GCG GTT TCA GCA ACA
     asn tyr pro ala ala tyr ser ser val val ala val ser ala thr 856  AAC GAA AAG AAT CAG CTT GCC TCC TTT TCA ACA ACT GGA GAT GAA
     asn glu lys asn gln leu ala ser phe ser thr thr gly asp glu 901  GTT GAA TTT TCA GCA CCG GGG ACA AAC ATC ACA AGC ACT TAC TTA
     val glu phe ser ala pro gly thr asn ile thr ser thr tyr leu 946  AAC CAG TAT TAT GCA ACG GGA AGC GGA ACA TCC CAA GCG ACA CCG
     asn gln tyr tyr ala thr gly ser gly thr ser gln ala thr pro 991  CAC GCC GCT GCC ATG TTT GCC TTG TTA AAA CAG CGT GAT CCT GCC
     his ala ala ala met phe ala leu leu lys gln arg asp pro ala 1036 GAG ACA AAC GTC CAG CTT CGC GAG ATG CGG AAA AAC ATC GTT
     glu thr asn val gln leu arg glu met arg lys asn ile val 1081 GAT CTT GGT ACC GCA GGC CGC GAT CAG CAA TTT GGC TAT GGC TTA
     asp leu gly thr ala gly arg asp gln gln phe gly tyr gly leu
```
              KpnI

FIG. 6-4

1126 ATC CAG TAT AAA GCA CAG TAT AAA GCA ACA GAT TCA GCG TAC GCA GCA
     ile gln tyr lys ala gln thr asp ser ala tyr ala ala 1171 GAG CAA GCG GTG AAA GCG GAA CAA ACA AAA GCA CAA ATC GAT
     glu gln ala val lys ala glu gln thr lys ala gln ile asp
     EcoRV 1216 ATC AAC AAA GCG CGA GAA CTC ATC AGC CAG CTG CCG AAC TCC GAC
     ile asn lys ala arg glu leu ile ser gln leu pro asn ser asp 1261 GCC AAA ACT GCC CTG CAC GAT AAA AGA CTG GAT AAA GTA CAG TCA TAC
     ala lys thr ala leu his asp lys arg leu asp lys val gln ser tyr 1306 AGA AAT GTA AAA GAT GCG AAA GAC GTC GCA AAG GCA GAA AAA
     arg asn val lys asp ala lys asp val ala lys ala glu lys 1351 TAT AAA ACA CAG CAA ACC GTT GAC ACA CAA ACT GCC ATC AAC
     tyr lys thr gln gln thr val asp thr gln thr ala ile asn 1396 AAG CTG CCA AAC GGA ACA GAC AAA AAG AAC CTT CAA AAA CGC TTA
     lys leu pro asn gly thr asp lys lys asn leu gln lys arg leu

FIG. 6-5

```
1441 GAC CAA GTA AAA CGA TAC ATC GCG TCA AAG CAA GCG AAA GAC AAA
     asp gln val lys arg tyr ile ala ser lys gln ala lys asp lys 1486 GTT GCG AAA GCG GAA AAA AGC AAG AAA ACA GAT GTG GAC AGC
     val ala lys ala glu lys ser lys lys thr asp val asp ser
              PstI
1531 GCA CAA TCA GCA ATT GGC AAG CTG CCT GCA AGT TCA GAA AAA ACG
     ala gln ser ala ile gly lys leu pro ala ser ser glu lys thr 1576 TCC CTG CAG AAA CGC CTT AAC AAA GTG AAG AGC ACC AAT TTG AAG
     ser leu gln lys arg leu asn lys val lys ser thr asn leu lys 1621 ACG GCA CAG CAA TCC GTA TCT GCG GCT GAA AAA TCA ACT GAT GCA
     thr ala gln gln ser val ser ala ala glu lys ser thr asp ala 1666 GCA AAT GCG GCA GCA CAA CAA TCA GCC GTC AAT CAG CTT CAA GCA
     ala asn ala ala ala lys ala gln ser ala val asn gln leu gln ala 1711 GGC AAG GAC AAA ACG GCA TTG CAA AAA CGG TTA GAC AAA GTG AAG
     gly lys asp lys thr ala leu gln lys arg leu asp lys val lys
```

FIG. 6-6

1756 AAA AAG GTG GCG GCT GAA GCA AAA GTG GAA ACT GCA AAG
     lys lys val ala ala glu ala lys val glu thr ala lys 1801 GCA AAA GTG AAG AAA GCG GAA AAA GAC AAA ACA AAG AAG
     ala lys val lys lys ala glu lys asp lys thr lys lys TCA AAG
     ser lys 1846 ACA TCC GCT CAG TCT GCA GTG AAT CAA TTA AAA GCA TCC AAT GAA
     thr ser ala gln ser ala val asn gln leu lys ala ser asn glu
                    PstI 1891 AAA ACA AAG CTG CAA AAA CGG CTG AAC GCC GTC AAA CCG AAA
     lys thr lys leu gln lys arg leu asn ala val lys pro lys 1936 AAG TAA CCAAAAACCTTTAAGATTGCATTCCAAGTCTTAAAGGTTTTTT
     lys ***

1994 CATTCTAAGA

FIG. 6-7

| Position | 2 | 3 | 4 | 5 | 6 | 7 | 8 | 9 | 10 |
|---|---|---|---|---|---|---|---|---|---|
| 5' - | ACA - | GAT - | GGA - | GTT - | GAA - | TGG - | AAT - | GTT - | GAT - |
|  | Thr - | Asp - | Gly - | Val - | Glu - | Trp - | Asn - | Val - | Asp - |

| 11 | 12 | 13 | 14 | 15 | 16 | 17 | 18 | 19 | 20 |
|---|---|---|---|---|---|---|---|---|---|
| CAA - | ATT - | GAT - | GCT - | CCG - | AAA - | GCT - | TGG - | GCT - | TTA - |
| Gln - | Ile - | Asp - | Ala - | Pro - | Lys - | Ala - | Trp - | Ala - | Leu - |

| 21 | 22 | 23 | 24 | 25 | 26 | 27 | 28 |  |  |
|---|---|---|---|---|---|---|---|---|---|
| GGA - | TAT - | GAT - | GGA - | ACA - | GGA - | ACA - | GTT - | 3' |  |
| Gly - | Tyr - | Asp - | Gly - | Thr - | Gly - | Thr - | Val - |  |  |

FIG. 8

The underlined portion is the approximate location of the RP-I gene on the PstI fragment.

The shaded box represents the region to which the RP-II "guess-mers" hybridized.

FIG. 10-1

```
-199  TAACAAACAGATAATTAGACCCATTTATTTGTGAGATTTTATCATTTCATATAT
      GGAAATTGAACGACGAAACGAAATTGTAATTCTGTAATTCTGTAATTCAGATTGTCTACAGTTAATA
      TACAGCGATGTTCTGACAAACCATTCATTATTAAAAGGAGGACGACACTTTTTTA
      AAAAGCATGTTGAAAAGGGGATGAAA
```

```
  +1  ATG AGG AAA AAA ACG AAA AAC AGA CTC ATC AGC TCT CTT TTA AGT
      met arg lys lys thr lys asn arg leu ile ser ser leu leu ser 46  ACA GTT GTC ATC AGT TCA CTG CTG TTT CCG GGA GCA GCC GGG GCA
      thr val val ile ser ser leu leu phe pro gly ala ala gly ala 91  AGC AGT AAA GTC ACC TCA CCT TCT GTT AAA AAG GAG CTT CAA TCT
      ser ser lys val thr ser pro ser val lys lys glu leu gln ser 136  GCG GAA TCC ATT CAA AAC AAG ATT TCG AGT TCA TTA AAG AAA AGC
      ala glu ser ile gln asn lys ile ser ser leu lys lys ser BglII
 181  TTT AAA AAG AAA GAA AAA ACG ACT TTT CTG ATT AAA TTT AAA GAT
      phe lys lys lys glu lys thr thr phe leu ile lys phe lys asp
```

FIG. 10-2

```
226  CTG GCT AAC CCA GAA AAA GCA GCG GCA AAA GCG GCT GTT AAA AAA GCG
     leu ala asn pro glu lys ala ala ala lys ala ala val lys lys ala 271  AAA TCG AAG AAG CTG TCT GCC GCT AAG ACG GAA TAT CAA AAG CGT
     lys ser lys lys leu ser ala ala lys thr glu tyr gln lys arg 316  TCT GCT GTT GTG TCA TCT TTA AAA GTC ACA GCC GAT GAA TCC CAG
     ser ala val val ser ser leu lys val thr ala asp glu ser gln 361  CAA GAT GTC CTA AAA TAC TTG AAC ACC CAG AAA GAT AAA GGA AAT
     gln asp val leu lys tyr leu asn thr gln lys asp lys gly asn 406  GCA GAC CAA ATT CAT TCT TAT TAT GTG GTG AAC GGG ATT GCT GTT
     ala asp gln ile his ser tyr tyr val val asn gly ile ala val 451  CAT GCC TCA AAA GAG GTT ATC GAA AAA GTG GTG CAG TTT CCC GAA
     his ala ser lys glu val ile glu lys val val gln phe pro glu
```

FIG. 10-3

```
496  GTG GAA AAG GTG CTT CCT AAT GAG AAA CGG CAG CTT TTT AAG TCA
     val glu lys val leu pro asn glu lys arg gln leu phe lys ser 541  TCC TCC CCA TTT AAT ATG AAA AAA GCA CAG AAA GCT ATT AAA GCA
     ser ser pro phe asn met lys lys ala gln lys ala ile lys ala
                                                         ClaI
586  ACT GAC GGT GTG GAA TGG AAT GTA GAC CAA ATC GAT GCC CCA AAA
     thr asp gly val glu trp asn val asp gln ile asp ala pro lys 631  GCT TGG GCA CTT GGA TAT GAT GGA ACT GGC ACG GTT GTT GCG TCC
     ala trp ala leu gly tyr asp gly thr gly thr val val ala ser 676  ATT GAT ACC GGG GTG GAA TGG AAT CAT CCG GCA TTA AAA GAG AAA
     ile asp thr gly val glu trp asn his pro ala leu lys glu lys 721  TAT GCG GGA TAT AAT CCT GAA AAT GAG CCT AAT GAA AAT GAA
     tyr arg gly tyr asn pro glu asn glu pro asn glu asn glu
```

FIG. 10-4

```
766  ATG AAC TGG TAT GAT GCC GTA GCA GAG GCA AGC CCT TAT GAT
     met asn trp tyr asp ala val ala gly glu ala ser pro tyr asp 811  GAT TTG GCT CAT GGA ACC CAC GTG ACA GGC ATG GTG GGC TCT
     asp leu ala his gly thr his val thr gly met val gly ser 856  GAA CCT GAT GGA ACA AAT CAA ATC GGT GTA GCA CCT GGC GCA AAA
     glu pro asp gly thr asn gln ile gly val ala pro gly ala lys 901  TGG ATT GCT GTT AAA GCG TTC TCT GAA GAT GGC ACT GAT GCT
     trp ile ala val lys ala phe ser glu asp gly thr asp ala 946  GAC ATT TTG GAA GCT GGT GAA TGG GTT TTA GCA CCA AAG GAC GCG
     asp ile leu glu ala gly glu trp val leu ala pro lys asp ala 991  GAA GGA AAT CCC CAC CCG GAA ATG GCT CCT GAT GTT GTC AAT AAC
     glu gly asn pro his pro glu met ala pro asp val val asn asn
```

FIG. 10-5

```
1036  TCA TGG GGA GGC TCT GGA CTT GAT GAA TGG TAC AGA GAC ATG
      ser trp gly gly ser gly leu asp glu trp tyr arg asp met 1081  GTC AAT GCC TGG CGT TCG GCC GAT ATT TTC CCT GAG TTT TCA GCG
      val asn ala trp arg ser ala asp ile phe pro glu phe ser ala 1126  GGG AAT ACG GAT CTC TTT ATT CCC GGC GGG CCT GGT TCT ALC GCA
      gly asn thr asp leu phe ile pro gly gly pro gly ser ile ala
                                                              EcoRV
1171  AAT CCG GCA AAC TAT CCA GAA TCG TTT GCA ACT GGA GCG ACT GAT
      asn pro ala asn tyr pro glu ser phe ala thr gly ala thr asp 1216  ATC AAT AAA AAG CTC GCT GAC TTT TCT CTT CAA GGG CCA TCT CCA
      ile asn lys lys leu ala asp phe ser leu gln gly pro ser pro 1261  TAT GAT GAA ATA AAG CCG GAA ATA TCT GCA CCG GGC GTT AAT ATT
      tyr asp glu ile lys pro glu ile ser ala pro gly val asn ile 1306  CGT TCA TCG GTT CCC GGT CAG ACA TAT GAG GAT GGT TGG GAC GGC
      arg ser ser val pro gly gln thr tyr glu asp gly trp asp gly
```

FIG. 10-6

```
1351  ACA TCA ATG GCA GGG CCG CAT GTA TCC GCT GTT GCT GCA CTG CTG
      thr ser met ala gly pro his val ser ala val ala ala leu leu 1396  AAA CAG GCG AAT GCC TCA CTT TCT GTT GAT GAG ATG GAG GAT ATA
      lys gln ala asn ala ser leu ser val asp glu met glu asp ile 1441  TTA ACC AGC ACG GCT GAA CCG CTC ACG GAT TCA ACA TTT CCT GAT
      leu thr ser thr ala glu pro leu thr asp ser thr phe pro asp 1486  TCA CCG AAT AAC GGA TAT GGC CAT GGT CTG GTG AAT GCT TTT GAT
      ser pro asn asn gly tyr gly his gly leu val asn ala phe asp 1531  GCT GTA TCC GCT GTT ACA GAT GGA TTA GGG AAA GCG GAA GGA CAA
      ala val ser ala val thr asp gly leu gly lys ala glu gly gln 1576  GTT TCT GTA GAG GGG GAT GAC CAA GAG CCT CCT GTC TAT CAG CAT
      val ser val glu gly asp asp gln glu pro pro val tyr gln his
```

FIG. 10-7

```
1621  GAG AAA GTA ACT GAA GCT GAA TAT GAA GGT GGC AGC CTA CCA CTG ACT
      gly lys val thr glu ala tyr glu gly gly ser leu pro leu thr 1666  TTG ACA GCT GAA GAC AAT GTG AGT GTG ACA TCT GTA AAG CTG TCC
      leu thr ala glu asp asn val ser val thr ser val lys leu ser 1711  TAC AAG CTT GAT CAA GGT GAA TGG ACA GAA ATA ACG GCT AAA CGA
      tyr lys leu asp gln gly glu trp thr glu ile thr ala lys arg 1756  ATC AGC GGT GAT CAT CTA AAA GGA ACG TAT CAG GCA GAG ATC CCA
      ile ser gly asp his leu lys gly thr tyr gln ala glu ile pro 1801  GAT ATA AAA GGA ACT AAA CTA AGC TAT AAG TGG ATG ATT CAC CAT
      asp ile lys gly thr lys leu ser tyr lys trp met ile his asp 1846  TTT GGC CAT GTC GTT TCG TCT GAC GTA TAC GAT GTA ACA GTG
      phe gly gly his val val ser ser asp val tyr asp val thr val
```

FIG. 10-8

```
1891  AAA CCA AGC ATC ACG GCG GGA TAT AAG CAG GAC TTT GAA ACT GCA
      lys pro ser ile thr ala gly tyr lys gln asp phe glu thr ala 1936  CCC GGC GGC TGG GTT GCG AGC GGA ACA AAT AAT AAC TGG GAA TGG
      pro gly gly trp val ala ser gly thr asn asn asn trp glu trp 1981  GGA GTT CCG TCA ACT GGC CCA AAT ACA GCA TCC GGA GAA AAA
      gly val pro ser thr gly pro asn thr ala ser gly glu lys 2026  GTA TAT GGA ACG AAT TTG ACA GAA ATT ATG CCA ACT CAG CAA ACA
      val tyr gly thr asn leu thr glu ile met pro thr gln gln thr 2071  TGA ACCTTGTTATGCCTCCTATTAAAGCACCTGATTCAGGAAGTCTGTTCCTTCAATT
      OPA
      TAAAAGCTGGCACAATTAGAGGATGATTTGATTACGGCTACGTTTTTGTTCTTCCGA
      AGGTGAAAAGAATTGGGAGCAGGCTGGTGTCTATACGGAAGCTCAAGCTGGACGACGAG
      AATGTTATCGGCTTATAAG
```

```
    1     2     3     4     5     6     7     8     9    10
   Val - Thr - Asn - Asp - Val - Phe - Asn - Asn - Ile - Gln -
   (4)   (4)   (2)   (2)   (4)   (2)   (2)   (2)   (3)   (2)
5'- CTG - ACA - AAC - GAC - GTG - TTT - AAC - AAC - ATC - CAG -

11    12    13    14    15
   Tyr - Trp - Ala - Asn - Gln
   (2)   (1)   (4)   (2)   (2)
   TAT - TGG - GCA - AAC - CAG - 3'
```

FIG. 11a

| | 1 | 2 | 3 | 4 | 5 | 6 | 7 | 8 | 9 | 10 |
|---|---|---|---|---|---|---|---|---|---|---|
| 5'— | Ala | Thr | Val | Gln | Leu | Ser | Ile | Lys | Tyr | Pro — |
| | (4) | (4) | (4) | (2) | (6) | (6) | (3) | (2) | (2) | (4) |
| | GCA | ACA | GTT | CAA | CTT | TCA | ATC | AAA | TAT | CCG |

| | 11 | 12 | 13 | 14 | 15 | 16 | 17 | 18 | 19 | 20 |
|---|---|---|---|---|---|---|---|---|---|---|
| | Asn | Thr | Ser | (Cys) | (Thr) | Tyr | (Gly) | Asn | Thr | Gly — |
| | (2) | (4) | (6) | (2) | (4) | (2) | (4) | (2) | (4) | (4) |
| | AAC | ACA | TCA | TGC | ACA | TAT | GGC | AAC | ACA | GGC |

| | 21 | 22 | 23 | 24 | 25 | 26 | 27 | 28 | 29 | 30 |
|---|---|---|---|---|---|---|---|---|---|---|
| | Phe | Leu | Val | Asn | Pro | | (Thr) | Val | Val | Thr — |
| | (2) | (6) | (4) | (2) | (4) | | (4) | (4) | (4) | (4) |
| | TTT | CTT | GTT | AAC | CCG | 3' | | | | |

31
Ala
(4)

FIG. 11b

```
 1     2     3     4     5     6     7     8     9    10
Thr - Thr - Asn - Ser - Ser - Ser - Pro - Val - Gly - Leu -
(4)   (4)   (2)   (6)   (6)   (6)   (4)   (4)   (4)   (6)

11    12    13    14    15    16    17    18    19    20
Ser - Ser - Ser - Val - Thr - Gly - Phe - Pro - Cys - Asp -
(6)   (6)   (6)   (4)   (4)   (4)   (2)   (4)   (2)   (2)

3' - TGT - CCG - AAA - GGC - ACG - CTG -

21    22    23    24    25    26    27    28    29    30
Lys - Thr - Phe - Gly - Thr - Met - Trp - Ser - Asp - Thr -
(2)   (4)   (2)   (4)   (4)   (1)   (1)   (6)   (2)   (4)

TTT - TGT - AAA - CCG - TGT - TAC - ACC - 5'

31    32    33    34    35    36
Lys - Pro - Ile - Asn - Ser - Arg
(2)   (4)   (3)   (2)   (6)   (6)
```

FIG. 11c

Probe BRT90  Probe 707

```
        GGACACTAAAGGAGGAGATGACAAA  ATG AAA TTA GTT CCA AGA TTC ACA
-26                                +1
                                   met lys leu val pro arg phe arg 25  AAA CAA TGG TTC GCT TAC TTA ACG GTT TTG TGT TTG GCT TTG GCA
     lys gln trp phe ala tyr leu thr val leu cys leu ala leu ala 70  GCA GCG GTT TCT TTT GGC GTA CCG GCA AAA GCA GAG AAC CCG
     ala ala val ser phe gly val pro ala lys ala glu asn pro 115  CAA ACT TCT GTA TCG AAT ACC GGT AAA GAA GCT GAT GCT ACG AAA
     gln thr ser val ser asn thr gly lys glu ala asp ala thr lys 160  AAC CAA ACG TCA AAA GCA GAT CAG GTT TCC GCC CCT TAT GAG GGA
     asn gln thr ser lys ala asp gln val ser ala pro tyr glu gly 205  ACC GGA AAA ACA AGT AAA TCG TTA TAC GGC GGC CAA ACG GAA CTG
     thr gly lys thr ser lys ser leu tyr gly gly gln thr glu leu 250  GAA AAA AAC ATT CAA ACC TTA CAG CCT TCG AGC ATT ATC GGA ACT     N-
     glu lys asn ile gln thr leu gln pro ser ser ile ile gly thr    terminus
```

FIG. 14-1

```
                                                                                    T94
295  GAT GAA CGC ACC AGA ATC TCC AGC ACG ACA TCT TTT CCA TAT AGA
     asp glu arg thr arg ile ser ser thr thr ser phe pro tyr arg 340  GCA ACC GTT CAA CTG TCA ATC AAG TAT CCC AAC ACT TCA AGC ACT
     ala thr val gln leu ser ile lys tyr pro asn thr ser ser thr 385  TAT GGA TGT ACC GGA TTT TTA GTC AAT CCA AAT ACA GTC GTC ACG
     tyr gly cys thr gly phe leu val asn pro asn thr val val thr 430  GCT GGA CAT TGT GTG TAC AGC CAG GAT CAT GGA TGG GCT TCG ACG
     ala gly his cys val tyr ser gln asp his gly trp ala ser thr 475  ATA ACC GCC GCG CCG GGC CGC AAT GGG TCG TCA TAT CCG TAC GGT
     ile thr ala ala pro gly arg asn gly ser ser tyr pro tyr gly 520  ACT TAT TCA GGC ACG ATG TTT TAC TCC GTC AAA GGA TGG ACG GAA
     thr tyr ser gly thr met phe tyr ser val lys gly trp thr glu 565  AGC AAA GAC ACC AAC TAT GAT TAC GGA GCT ATT AAA TTA AAC GGT
     ser lys asp thr asn tyr asp tyr gly ala ile lys leu asn gly
```

FIG. 14-2

```
                                                                              T92
610 TCT CCT GGA AAC ACG GTT GGC TGG TAC CGG ACT ACA AAC
    ser pro gly asn thr val gly trp tyr arg thr thr asn 655 AGC AGT CCC GTG GGC CTT TCC TCG ACA GGA TTC CCA
    ser ser pro val gly leu ser ser val thr gly phe pro 700 TGT GAC AAA ACC TTT GGC ACG ATG TGG TCT GAT ACA AAG CCG AAT
    cys asp lys thr phe gly thr met trp ser asp thr lys pro ile 745 CGC TCC GCT GAA ACG TAT AAG CTG ACC TAT ACA ACC GAT ACG TAC
    arg ser ala glu thr tyr lys leu thr tyr thr thr asp thr tyr 790 GGC TGC CAA AGC GGC TCG CCT GTT TAT CGA AAC TAC AGT GAT ACA
    gly cys gln ser gly ser pro val tyr arg asn tyr ser asp thr 835 GGG CAG ACA GCT ATT GCC ATT CAC ACG AAC GGA TCG TCA TAT
    gly gln thr ala ile ala ile his thr asn gly ser ser tyr
```

FIG. 14-3

880 AAC TTG GGA ACA AGG GTG ACG AAC GAT GTA TTC AAC AAT ATT CAA T90
    asn leu gly thr arg val thr asn asp val phe asn asn ile gln 925 TAT TGG GCA AAT CAA TAA ATACAGCAAACTAGCCATATTCATGTCTAT
    tyr trp ala asn gln OCH

FIG. 14-4

PROTEASE DELETION

This is a divisional of copending application Ser. No. 07/579,401 filed on Sep. 7, 1990, which is a continuation-in-part of application Ser. No. 07/396,521 filed Aug. 21, 1989, now abandoned, which is a continuation-in-part of application Ser. No. 07/347,428 filed May 4, 1989, now abandoned, which is a continuation-in-part of application Ser. No. 07/273,423 filed Nov. 18, 1988, now abandoned.

BACKGROUND OF THE INVENTION

This invention relates to Bacillus strains useful for the expression and secretion of desired polypeptides (as used herein, "polypeptide" means any useful chain of amino acids, including proteins).

Bacillus strains have been used as hosts to express heterologous polypeptides from genetically engineered vectors. The use of a Gram positive host such as Bacillus avoids some of the problems associated with expressing heterologous genes in Gram negative organisms such as *E. coli*. For example, Gram negative organisms produce endotoxins which may be difficult to separate from a desired product. Furthermore, Gram negative organisms such as *E. coli* are not easily adapted for the secretion of foreign products, and the recovery of products sequestered within the cells is time-consuming, tedious, and potentially problematic. In addition, Bacillus strains are non-pathogenic and are capable of secreting proteins by well-characterized mechanisms.

A general problem in using Bacillus host strains in expression systems is that they produce large amounts of proteases which can degrade heterologous polypeptides before they can be recovered from the culture media. The proteases which are responsible for the majority of this proteolytic activity are produced at the end of the exponential phase of growth, under conditions of nutrient deprivation, as the cells prepare for sporulation. The two major extracellular proteases an alkaline serine protease (subtilisin), the product of the apr gene, and a neutral metalloprotease, the product of the npr gene, are secreted into the medium, whereas the major intracellular serine protease, Isp-l, is produced within the cells. Other investigators have created genetically altered Bacillus strains that produce below-normal levels of one or more of these three proteases, but these strains still produce high enough levels of protease to cause the degradation of heterologous gene products prior to purification.

Stahl et al. (J. Bact., 1984, 158:411) disclose a Bacillus protease mutant in which the chromosomal subtilisin structural gene was replaced with an in vitro derived deletion mutation. Strains carrying this mutation produced only 10% of the wild-type extracellular serine protease activity. Yang et al. (J. Bact., 1984, 160:15) disclose a Bacillus protease mutant in which the chromosomal neutral protease gene was replaced with a gene having an in vitro derived deletion mutation. Fahnestock et al. (WO 86/01825) describe Bacillus strains lacking subtilisin activity which were constructed by replacing the native chromosomal gene sequence with a partially homologous DNA sequence having an inactivating segment inserted into it. Kawamura et al. (J. Bact., 1984, 160:442) disclose Bacillus strains carrying lesions in the npr and apr genes and expressing less than 4% of the wild-type level of extracellular protease activity. Koide et al. (J. Bact., 1986, 167:110) disclose the cloning and sequencing of the isp-l gene and the construction of an Isp-l negative mutant by chromosomal integration of an artificially deleted gene.

Genetically altered strains which are deleted for the extracellular protease genes (apr and npr) produce significantly lower levels of protease activity than do wild-type Bacillus strains. These bacteria, when grown on medium containing a protease substrate, exhibit little or no proteolytic activity, as measured by the lack of appearance of a zone of clearing (halo) around the colonies. Some heterologous polypeptides and proteins produced from these double mutants are, nevertheless, substantially degraded prior to purification, although they are more stable than when produced in a wild-type strain of Bacillus.

Summary of the Invention

The invention provides improved Bacillus cells containing mutations in one or more of three previously uncharacterized protease genes; the cells also preferably contain mutations in the apr and npr genes that encode the major extracellular proteases, resulting in the inhibition by the cells of production of these extracellular proteases. The mutations of the invention include a mutation in the epr gene which inhibits the production by the cell of the proteolytically active epr gene product, a mutation in the gene (herein, the "RP-I" gene) encoding residual protease I (RP-I) which inhibits the production by the cell of proteolytically active RP-I, and a mutation in the gene (herein, the "RP-II" gene) encoding residual protease II (RP-II). The proteases encoded by the epr gene and RP-II genes are novel proteins. Most preferably, the mutations of the invention are deletions within the coding region of the genes, including deletion of the entire coding region; alternatively, a mutation can consist of a substitution of one or more base pairs for naturally occuring base pairs, or an insertion within the protease coding region.

The Bacillus cells of the invention may also contain a mutation in the isp-l gene encoding intracellular serine protease I and may in addition contain a mutation which blocks sporulation and thus reduces the cell's capacity to produce sporulation-dependent proteases; preferably, this mutation blocks sporulation at an early stage but does not eliminate the cell's ability to be transformed by purified DNA; most preferably, this mutation is the spoOA mutation (described below). The invention further provides a method for producing stable heterologous polypeptides in a Bacillus host cell by modifying the host to contain mutations in the apr and npr genes and in one or more of the genes including the epr gene, the RP-I gene, and the RP-II gene.

The invention also features purified DNA, expression vectors containing DNA, and host Bacillus cells transformed with DNA encoding any of the proteases RP-I, RP-II, or the product of the epr gene; preferably, such DNA is derived from *Bacillus subtilis*.

The invention also features the isolation of substantially pure Epr, residual protease I (RP-I), and another previously uncharacterized protease called residual protease II (RP-II), and characterization of the RP-I and RP-II proteases; as used herein, "substantially pure" means greater than 90% pure by weight.

The terms "epr gene", "RP-I gene", and "RP-II gene" herein mean the respective genes corresponding to these designations in *Bacillus subtilis,* and the evolutionary homologues of those genes in other Bacillus species, which homologues, as is the case for other Bacillus proteins, can be expected to vary in minor respects from species to species. The RP-I and RP-II genes of *B. subtilis* are also designated, respectively, the bpr and mpr genes. In many cases, sequence homology between evolutionary homologues is great enough so that a gene derived from one species can be used as a hybridization probe to obtain the evolutionary homologue from another species, using standard techniques. In addition, of course, those terms also include genes in which base changes have been made which, because of the redundancy of the genetic code, do not change the encoded amino acid residue.

Using the procedures described herein, we have produced Bacillus strains which are significantly reduced in their ability to produce proteases, and are therefore useful as hosts for the expression, without significant degradation, of heterologous polypeptides capable of being secreted into the culture medium. We have found that the Bacillus cells of the invention, even though containing several mutations in genes encoding related activities, are not only viable but healthy.

Any desired polypeptide can be expressed according to the invention, e.g., medically useful proteins such as hormones, vaccines, antiviral proteins, antitumor proteins, antibodies or clotting proteins; and agriculturally and industrially useful proteins such as enzymes or pesticides, and any other polypeptide that is unstable in Bacillus hosts that contain one or more of the proteases inhibited according to the present invention.

Other features and advantages of the invention will be apparent from the following description of the preferred embodiments thereof, and from the claims.

Description of Preferred Embodiments

The drawings will first be briefly described.

DRAWINGS

FIG. 6 is the DNA sequence of the epr gene.

FIG. 8 is the amino acid sequence of the first 28 residues of RP-I and the corresponding DNA sequence of the probe used to clone the RP-I gene.

FIGS. 10-1, 10-2, 10-3, 10-4, 10-5, 10-6, 10-7, and 10-8 are the DNA sequence of DNA encoding RP-I protease.

FIGS. 11a, b, and c are the amino acid sequence of three internal RP-II fragments (a, b, c), and the nucleotide sequence of three guess-mers used to clone the gene (a), (b) and (c).

Figure 12A:
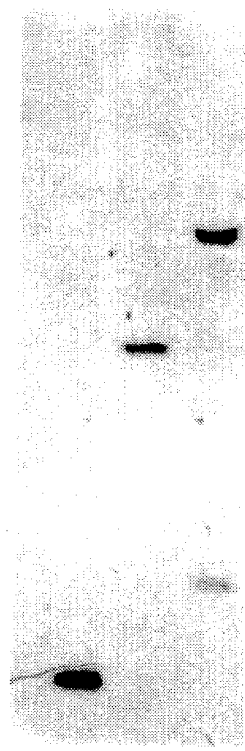
Figure 12B:
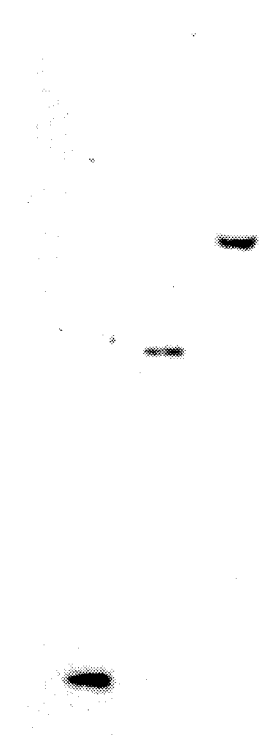

FIG. 12 is a Southern blot of GP241 chromosomal DNA probed with BRT90 and 707.

Figure 13A:
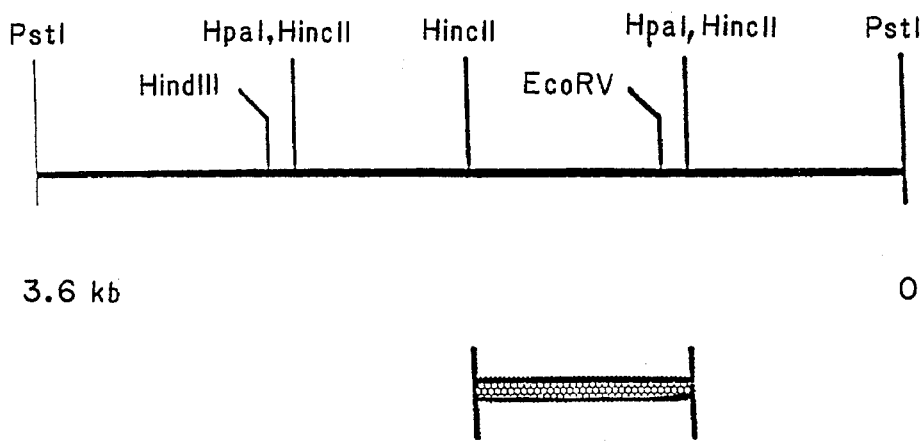
Figure 13B:
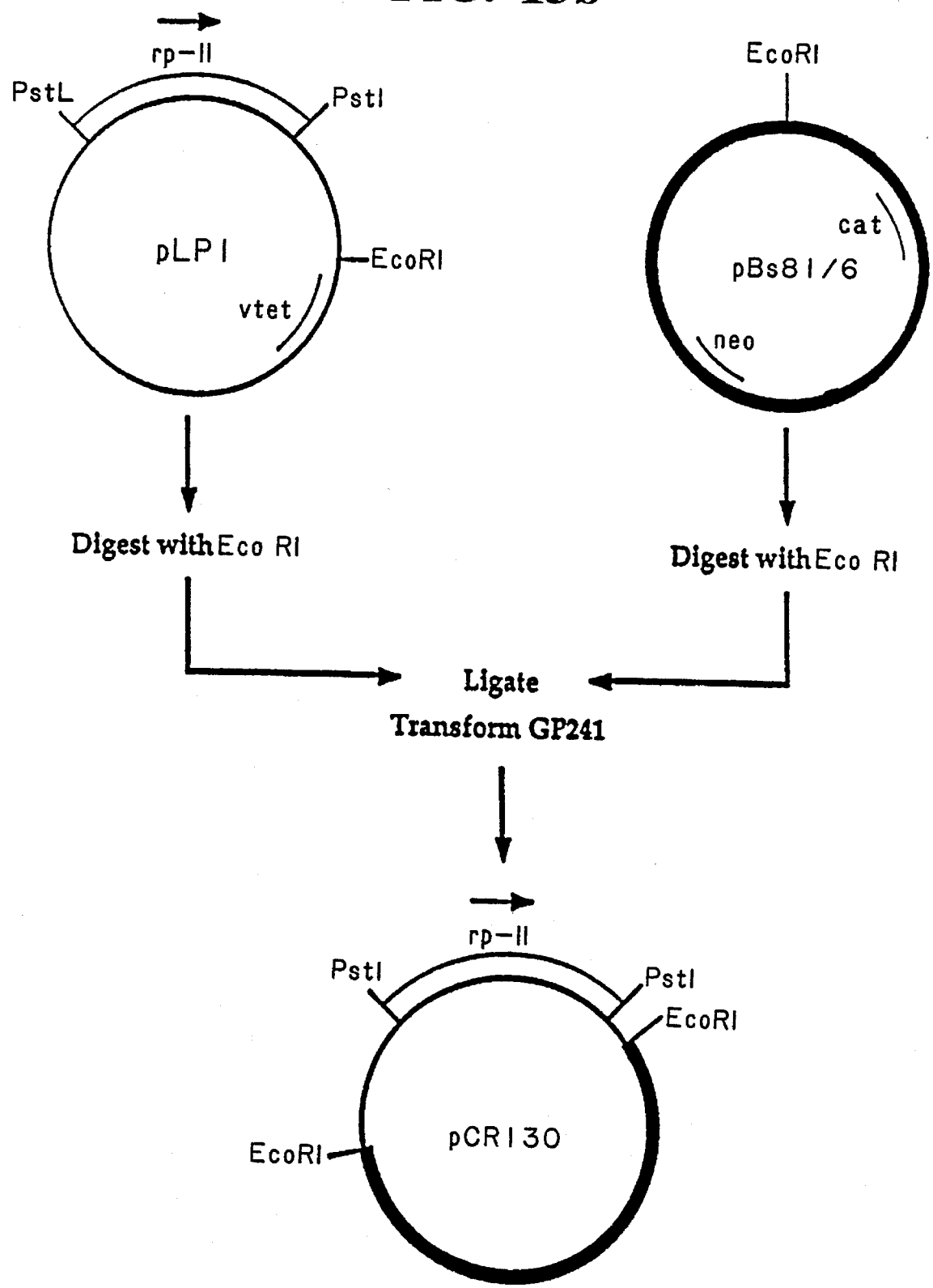
Figure 13C:
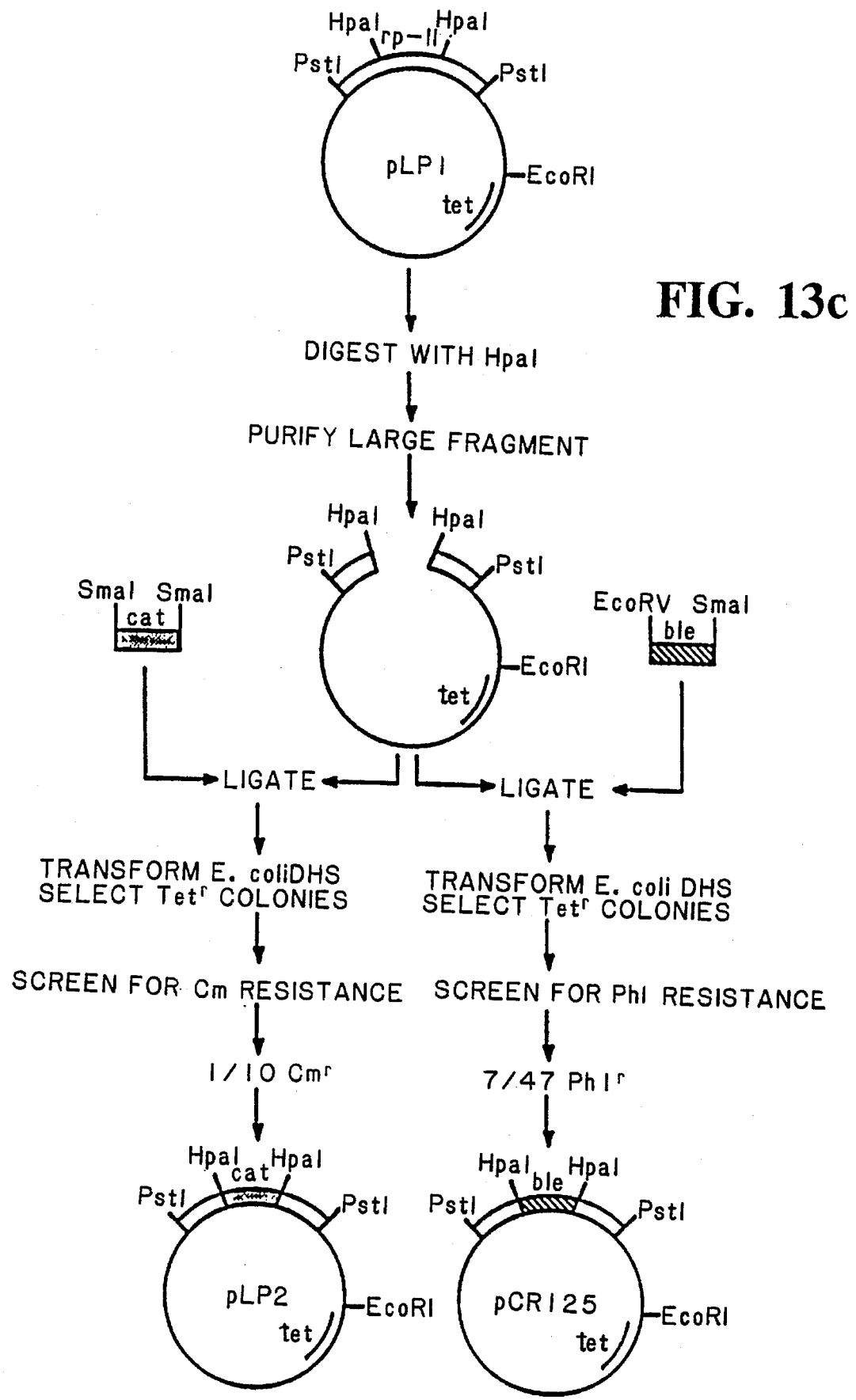

FIG. 13a–c are a diagram of (a) a restriction map of the 3.6 kb PstI insert of pLPI, (b) the construction of the deleted RP-II gene and (c) the plasmid used to create an RP-II deletion in the Bacillus chromosome.

FIG. 14 is the DNA sequence of DNA encoding RP-II.

GENERAL STRATEGY FOR CREATING PROTEASE DELETED BACILLUS STRAINS

The general strategy we followed for creating a Bacillus strain which is substantially devoid of proteolytic activity is outlined below.

A deletion mutant of the two known major extracellular protease genes, apr and npr, was constructed first. The isp-l gene encoding the major intracellular protease was then deleted to create a triple protease deletion mutant. The spoOA mutation was introduced into either the double or triple deletion mutants to significantly reduce any sporulation dependent protease activity present in the cell. A gene encoding a previously unknown protease was then isolated and its entire nucleotide sequence was determined. The gene, epr, encodes a primary product of 645 amino acids that is partially homologous to both subtilisin (Apr) and the major internal serine protease (Isp-l) of *B. subtilis*. A deletion of this gene was created in vitro and introduced into the triple protease deleted host. A deletion in a newly identified gene encoding residual protease RP-I was then introduced to create a strain of *B. subtilis* having substantially reduced protease activity and expressing only the RP-II activity. RP-II has been purified and a portion of the amino acid sequence was determined for use in creating the nucleic acid probes which were used to clone the gene encoding this protease. Upon cloning the gene, it was possible to create a Bacillus strain which contains a deletion in the RP-II gene and is thus incapable of producing RP-II.

Detailed procedures for construction of the protease gene deletions and preparation of Bacillus strains exhibiting reduced protease activity are described below.

General Methods

Our methods for the construction of a multiply deleted Bacillus strain are described below. Isolation of *B. subtilis* chromosomal DNA was as described by Dubnau et al., (1971, J. Mol. Biol., 56: 209). *B. subtilis* strains were grown on tryptose blood agar base (Difco Laboratories) or minimal glucose medium and were made competent by the procedure of Anagnostopoulos et al., (J. Bact., 1961, 81: 741). *E. coli* JM107 was grown and made competent by the procedure of Hanahan (J. Mol. Biol., 1983, 166: 587). Plasmid DNA from *B. subtilis* and *E. coli* were prepared by the lysis method of Birnboim et al. (Nucl. Acid. Res., 1979, 7: 1513). Plasmid DNA transformation in *B. subtilis* was performed as described by Gryczan et al., (J. Bact., 1978, 134: 138).

Protease Assays

Two different protease substrates, azocoll and casein (Labelled either with $^{14}$C or the chromophore resorufin), were used for protease assays, with the casein substrate being more sensitive to proteolytic activity. Culture supernatant samples were assayed either 2 or 20 hours into stationary phase. Azocoll-based protease assays were performed by adding 100 ul of culture supernatant to 900 ul of 50 mM Tris, pH 8, 5 mM $CaCl_2$, and 10 mg of azocoll (Sigma), a covalently modified, insoluble form of the protein collagen which releases a soluble chromophore when proteolytically cleaved. The solutions were incubated at 37° C. for 30 minutes with constant shaking. The reactions were then centrifuged to remove the insoluble azocoll and the $A_{520}$ of the solution determined. Inhibitors were pre-incubated with the reaction mix for 5 minutes at 37° C. Where a very small amount of residual protease activity was to be measured, $^{14}C$-casein or resorufin-labelled casein was used as the substrate. In the $^{14}C$-casein test, culture supernatant (100 ul) was added to 100 ul of 50 mM Tris, 5 mM $CaCl_2$ containing $1\times10^5$ cpm of $^{14}C$-casein (New England Nuclear). The solutions were incubated at 37° C. for 30 minutes. The reactions were then placed on ice and 20 ug of BSA were added as carrier protein. Cold 10% TCA (600 ul) was added and the mix was kept on ice for 10 minutes. The solutions were centrifuged to spin out the precipitated protein and the supernatants counted in a scintillation counter. The resorufin-labelled casein assay involved incubation of culture supernatant with an equal volume of resorufin-labelled casein in Tris=Cl buffer, pH 8.0, at 37° C. for various times. Following incubation, unhydrolyzed substrate was precipitated with TCA and the resulting chromogenic supernatant was quantitated spectrophotometrically.

Deletion of the Npr Gene

According to Yang et al. (J. Bact., 1984, 160: 15), the npr gene is contained within overlapping EcoRI and HindIII restriction fragments of *B. subtilis* DNA, and a majority of the gene sequence is located on the 2.4 kb HindIII fragment. This fragment was chosen for creation of the npr deletion.

An individual clone containing the 2.4 kb HindIII fragment was isolated from a clone bank of genomic HindIII fragments prepared as follows. Chromosomal DNA was isolated from B. subtilis strain IS75, digested with HindIII and size fractionated by electrophoresis on a 0.8% agarose gel. DNA in the 2–4 kb size range was electroeluted from the gel. The purified DNA was ligated to HindIII digested and alkaline phosphatase treated pUC9 DNA (an *E. coli* replicon commercially available from Bethesda Research Labs, Rockville, Md.), transformed into competent cells of *E. coli* strain JM107, and plated on LB+50 ug/ml ampicillin resulting in 1000 $Amp^R$ colonies.

Figure 1:
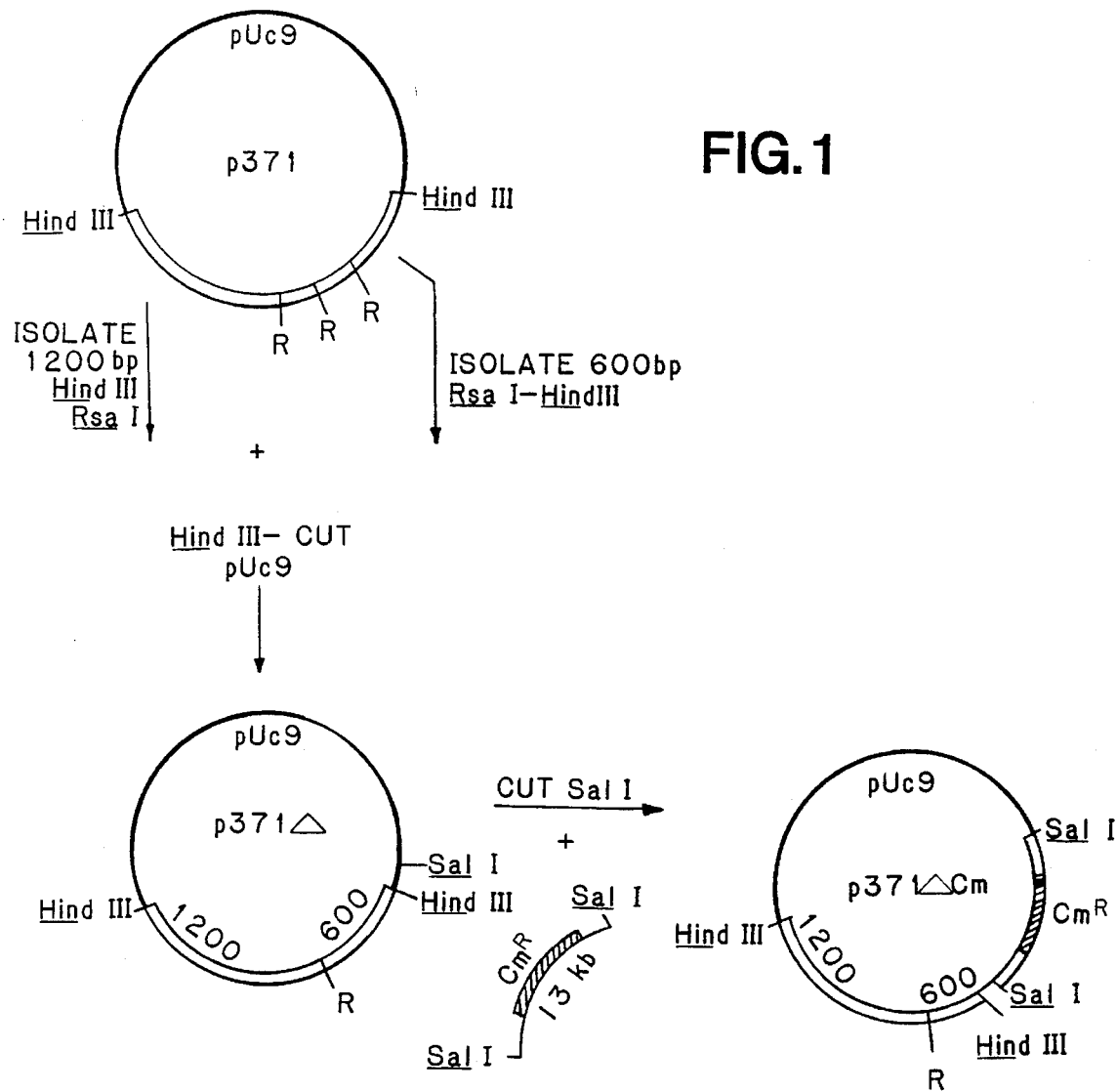
FIG. 1 is a series of diagrammatic representations of the plasmids p371 and p371Δ, which contain a 2.4 kb HindIII insert encoding the *Bacillus subtilis* neutral protease gene and the same insert with a deletion in the neutral protease gene, respectively, and p371ΔCM, which contains the Bacillus cat gene.

Colonies containing the cloned neutral protease gene fragment were identified by standard colony hybridization methods (Maniatis et al., 1983, "Molecular Cloning, A Laboratory Manual", Cold Spring Harbor, New York). Briefly, transformants are transferred to nitrocellulose filters, lysed to release the nucleic acids and probed with an npr specific probe. A 20 base oligonucleotide complementary to the npr gene sequence between nucleotides 520 and 540 (Yang et al., supra) was used as the probe. The sequence is 5'GGCACGCTTGTCTCAAGCAC 3'. A representative clone containing the 2.4 kb HindIII insert was identified and named p371 (FIG. 1).

A deleted form of the npr gene in p371 was derived in vitro. A 580 bp internal RsaI fragment was deleted by digesting p371 DNA with RsaI and HindIII. The 600 bp HindIII-RsaI fragment spanning the 5' end of the gene and the 1220 bp RsaI-HindIII fragment spanning the 3' end of the gene (see FIG. 1) were isolated and cloned into HindIII and alkaline phosphatase treated pUC9. This resulted in the deletion of the center portion of the npr gene. The ligated DNA was transformed into *E. coli* JM107. A clone having the desired deletion within the npr gene was identified by restriction enzyme analysis. This plasmid is designated p371Δ.

A gene encoding a selectable marker was included on the vector to facilitate the selection of integrants in Bacillus. The Bacillus cat gene, encoding resistance to chloramphenicol ($Cm^r$), was isolated from plasmid pMI1101 (Youngman et al., 1984, Plasmid 12:1–9) on a 1.3 kb SalI fragment and cloned into the SalI site of p371Δ. This DNA was transformed into *E. coli* JM107 and transformants were screened for chloramphenicol resistance. A representative plasmid containing both the deleted npr gene and the cat gene was named p371ΔCm (FIG. 1).

The vector p371ΔCm was derived from the *E. coli* replicon pUC19 and is therefore unable to replicate in a Bacillus host. The wild-type npr gene in the chromosome of the recipient host was exchanged for the deleted npr gene contained on the vector by reciprocal recombination between homologous sequences. The $Cm^r$ marker gene enabled the selection of cells into which the vector, inclusive of the protease gene sequence, had integrated.

Vector sequences that integrated with the deleted npr gene were spontaneously resolved from the chromosome at a low frequency, taking a copy of the npr gene along with them. Retention of the deleted protease gene in the chromosome was then confirmed by assaying for the lack of protease activity in the $Cm^s$ segregants.

Specifically, competent *B. subtilis* IS75 cells were transformed with p371ΔCm and selected for $Cm^r$. Approximately 2000 colonies, which had presumably integrated the deleted npr gene adjacent to, or in place of, the wild type gene, were selected which were resistant to chloramphenicol. Approximately 25% of the colonies formed smaller zones of clearing on starch agar indicating that the wild-type gene had been replaced with the deleted form of the gene. No neutral protease, activity was detected in supernatants from these cell cultures. In contrast, high levels of neutral protease activity were assayed in culture fluids from wild type IS75 cells. Segregants which contained a single integrated copy of the deleted protease gene, but which had eliminated the vector sequences were then selected as follows.

A culture of $Cm^r$ colonies was grown overnight in liquid media without selection then plated onto TBAB media. These colonies were then replicated onto media containing chloramphenicol and those that did not grow in the presence of chloramphenicol were identified and selected from the original plate. One such Npr negative colony was selected and designated IS75NΔ.

Deletion within the npr gene in IS75NΔ was confirmed by standard Southern blot analysis (Southern, 1977, J. Mol. Biol. 98: 503) of HindIII digested DNA isolated from *B. subtilis* IS75N and IS75NΔ probed with the $^{32}P$-labelled npr-specific oligonucleotide. The probe hybridized with a 2.4 kb HindIII fragment in wild-type IS75N DNA and with a 1.8 kb fragment in IS75N Δ DNA indicating that 600 bp of the npr gene were deleted in IS75NΔ (see FIG. 2).

Deletion of the Apr Gene

Figure 3:
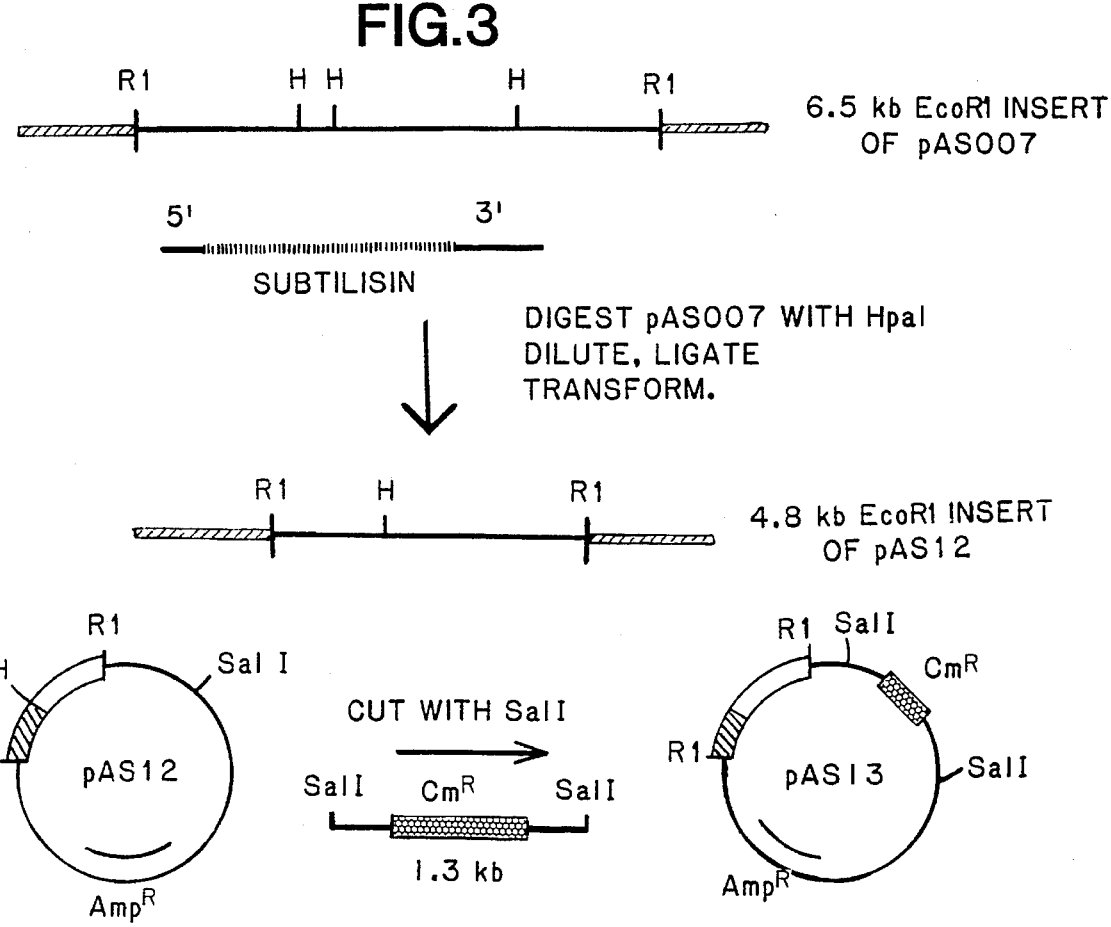
FIG. 3 is a representation of the 6.5 kb insert of plasmid pAS007, which encodes the *Bacillus subtilis* subtilisin gene, and the construction of the deletion. plasmid pAS13.

To clone the subtilisin gene (apr) a genomic library from IS75 DNA was first prepared. Chromosomal DNA was isolated and digested with EcoRI and separated by electrophoresis through a 0.8% agarose gel. Fragments in the 5–8 kb size range were purified by electroelution from the gel. The fragments were ligated with EcoRI digested pBR328 DNA (publicly available from New England BioLabs) and transformed into competent E. coli JM107 cells. Transformants were screened for plasmids containing apr gene inserts by hybridizing with a synthetic $^{32}$P-labelled 17-mer oligonucleotide probe which was complementary to the apr gene sequence between nucleotides 503 and 520 (Stahl et al., 1984, J. Bact. 158: 411). A clone with a 6.5 kb EcoRI insert that hybridized with the probe was selected and named pAS007 (FIG. 3). The 6.5 kb fragment contained the entire coding sequence of the subtilisin gene.

A mutant of the apr gene was created by deleting the two internal HpaI fragments (FIG. 3). pAS007 was first digested with HpaI and then recircularized by ligating in a dilute solution (5 ug/ml) to eliminate the two HpaI fragments. Approximately 200 Amp$^r$ colonies arose following transformation of JM107 cells. One of these transformants contained a 4.8 kb EcoRI insert with one internal HpaI site. It was designated pAS12. The deletion in the apr gene extended 500 bp beyond the 3' end of the gene, however this DNA apparently did not contain any genes that were essential to B. subtilis.

A 1.3 kb SalI fragment containing the Bacillus cat gene was cloned into the SalI site of pAS12 (described above) for selection of integrants in the Bacillus host chromosome. The plasmid DNA was transformed into E. coli JM107, plated on media containing ampicillin and approximately 50 Amp$^r$ colonies were recovered and replica plated onto media containing 7.5 ug/ml chloramphenicol. Three of the 50 colonies were Cm$^r$. Plasmid DNA was isolated from these three clones and analyzed by restriction digestion. One of the plasmids had the desired restriction pattern and was named pAS13 (FIG. 3).

To promote integration of the deleted protease gene into the B. subtilis chromosome, pAS13 was introduced into strain IS75NΔ and selected for Cm$^r$ transformants. The transformants were then screened for replacement of the wild-type apr gene with the deleted gene by plating on TBAB plates containing 5 ug/ml Cm and 1.5% casein. Several of the colonies which did not produce halos were selected for loss of the Cm$^r$ gene as described above. A representative transformant was chosen and designated GP199.

Protease activity was assayed in the culture fluids from the double protease deleted strain, as well as in the strain having only the deleted neutral protease gene. Protease activity in Npr$^-$,Apr$^-$ mutant cells was approximately 4–7% of wild type levels whereas the Npr$^-$ mutant exhibited higher levels of protease activity.

amyE Mutation

Protease deficient strains were tested in connection with the production of a Bacillus amylase. To assay the levels of amylase produced by various plasmid constructs it was necessary to introduce a mutant amylase gene into the host in place of the wild type gene, This step is not essential to the present invention and does not affect the level of protease activity; it was performed only because plasmid encoded amylase levels could not be determined in the presence of the chromosomally encoded amylase. The amyE allele was transformed from B. subtilis strain JF206 (trpC2, amyE) into GP199 by a transformation/selection process known as congression. This process relies on the ability of competent B. subtilis cells to be transformed by more than one piece of chromosomal DNA when the transforming DNA is provided in excess. The process involves initial selection of competent cells in the population by assaying for expression of a selectable marker gene which subsequently facilitates screening for co-transfer of an unselectable marker, such as inability to produce amylase.

Total chromosomal DNA was isolated from JF206 or a similar strain containing an amy E mutation. Saturating concentrations (~1ug) were transformed into competent GP199 (met$^-$,leu$^-$,his$^-$) and His$^+$ transformants were selected on minimal media supplemented with methionine and leucine. The transformants were screened for an amylase minus phenotype on plates having a layer of top agar containing starch-azure. Five percent of the His$^+$ colonies were unable to produce halos indicating that the amylase gene was defective. One such transformant was assayed for the protease-deficient phenotype and was designated GP200.

Supernatant samples from cultures of the double protease mutant were assayed for protease activity using azocoll as the substrate. When assayed on this substrate, protease activity in the double protease mutant strain was 4% of wild type levels. When the more sensitive substrate $^{14}$C-casein was used in the protease assay, the double mutant displayed 5–7% of the wild type B. subtilis activity. Although protease activity in this strain was low, we discovered that certain heterologous gene products produced by these protease deficient cells were not stable, indicating the presence of residual protease activity. We then sought to identify and mutate the gene(s) responsible for the residual protease activity.

In order to characterize the residual protease activity, a number of known protease inhibitors were tested for their ability to reduce protease levels in cultures of the double protease mutant strain. PMSF (phenylmethylsulfonyl flouride), a known inhibitor of serine protease activity, was found to be the most effective. The addition of PMSF to growing cultures of Apr$^-$Npr$^-$ Bacillus cells successfully increased the stability of heterologous peptides and proteins synthesized in and secreted from these cells. These results indicated that at least a portion of the residual degradative activity was due to a serine protease.

Subtilisin is the major serine protease to be secreted by B. subtilis; however, the serine protease encoded by the isp-1 gene (ISP-1) has been shown to accumulate intracellularly during sporulation (Srivastava et al., 1981, Arch. Microbiol., 129: 227). In order to find out if the residual protease activity was due to Isp-1, a deleted version of the isp-1 gene was created in vitro and incorporated into the double-protease deleted strain.

Deletion of the Isp-1 Gene

The isp-1 gene is contained within a 2.7 kb BamHI fragment of B. subtilis chromosomal DNA (Koide et al., 1986, J. Bact., 167:110). Purified DNA was digested with BamHI and fragments in the 2.7 kb size range were electroeluted from an agarose gel, ligated into BamHI digested pBR328 and transformed into E. coli JM107 cells. One Amp$^r$ colony that produced a halo on LB media containing 1% casein was selected and named pISP-1. Restriction analysis of the DNA indicated that pISP-1 carried a 2.7 kb BamHI insert which hybridized with a synthetic 25 base $^{32}$P-labeled oligonucleotide probe [5'ATGAATGGT-GAAATCCGCTTGATCC 3'] complementary to the isp-1 gene sequence (Koide et al, supra). The restriction pattern generated by SalI and EcoRI digestions confirmed the presence of the isp-1 gene in pISP-1.

Figure 4:
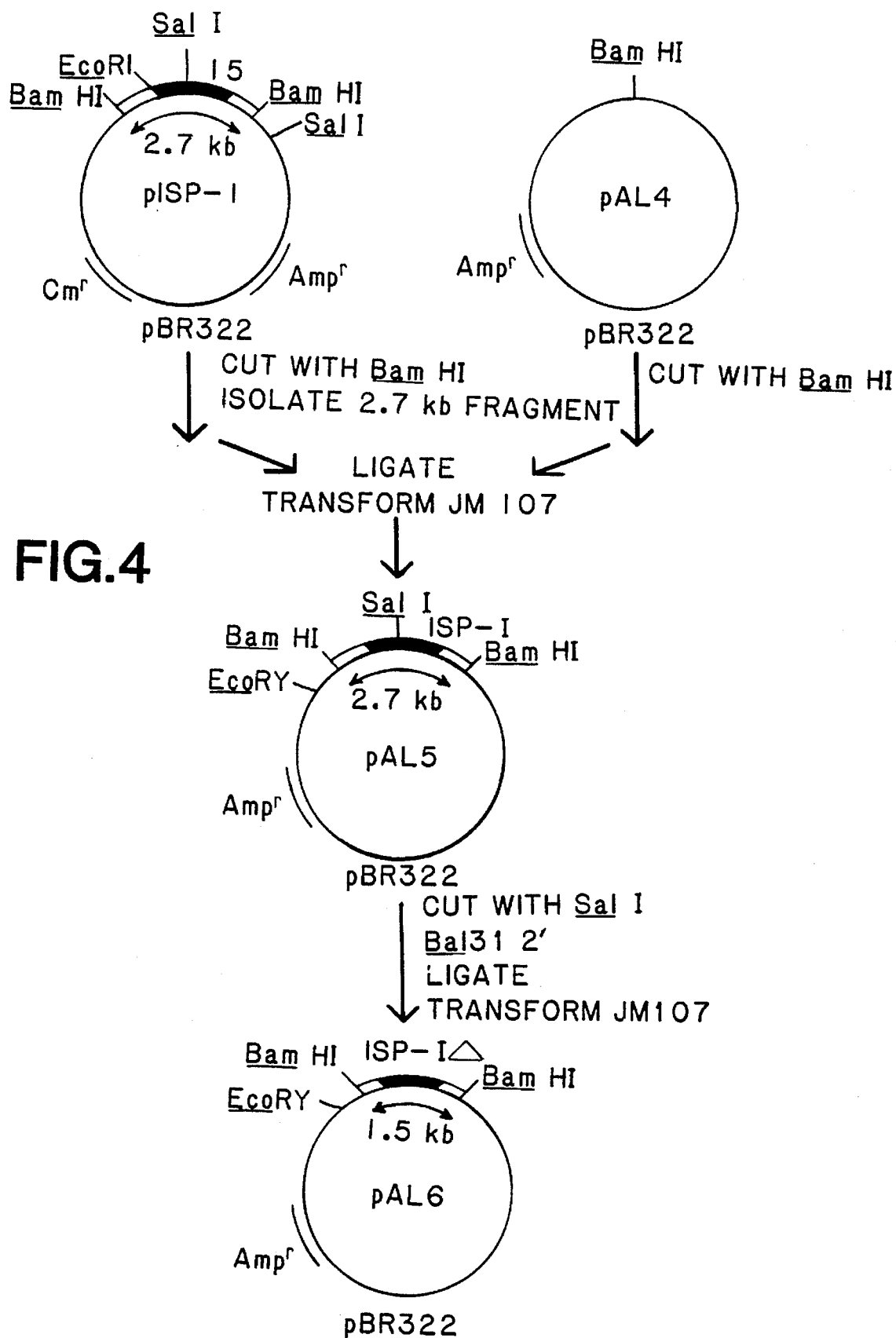
FIG. 4 is a representation of the plasmid pISP-1 containing a 2.7 kb BamHI insert which encodes the intracellular serine protease ISP-1, and the construction of the ISP-1 deletion plasmid pAL6.

A deletion was created within the isp-1 gene by taking advantage of a unique SalI site located in the center of the gene. Because there was an additional SalI site in the vector, the 2.7 kb BamHI gene insert was first cloned into the BamHi site of a derivative of pBR322 (pAL4) from which the SalI site had been eliminated (FIG. 4). The resulting plasmid, pAL5, therefore had a unique SalI site within the isp-1 gene. pAL5 DNA was digested with SalI, treated with Bal31 exonuclease for five minutes at 37° C. to delete a portion of the gene sequence, and religated. The DNA was transformed into JM107 and resulting Amp colonies were screened for a BamHI insert of reduced size. A plasmid with a 1.2 kb deletion within the BamHI insert was selected and named pAL6 (FIG. 4).

The cat gene was purified from the *E. coli* plasmid pMI1101 on a SalI fragment as above and cloned into pAL6 at the EcoRV site. The resulting DNA was transformed into the double protease mutant strain (GP200) and integrants containing the deleted ISP-1 gene were selected as described above. The triple-protease deleted strain is called GP208 (aprΔ, nprΔ, isp-1Δ). Using a casein substrate, protease activity was measured in the triple-mutant strain (Apr⁻,Npr⁻,Isp-1⁻) and found to be 4% of the wild type level, about the same as the double mutant strain.

The remaining 4% residual protease activity was apparently due either to a, previously described esterase called bacillopeptidase F (Roitsch et al., 1983, J. Bact., 155: 145), or to previously unknown and unidentified protease gene(s).

Introduction of a Sporulation Mutation

Because it had been shown that the production of certain proteases was associated with the process of sporulation in *B. subtilis,* we reasoned that it may be useful to include a mutation which blocked sporulation in our protease deficient hosts and thus further reduce sporulation-dependent protease production in these strains. Mutations that block the sporulation process at stage 0 reduce the level of protease produced, but do not eliminate the ability of the cells to be transformed by purified DNA. spoOA mutations have been shown to be particularly efficient at decreasing protease synthesis (Ferrari et al., 1986, J. Bact. 166:173).

We first introduced the spoOA mutation into the double protease deficient strain as one aspect of our strategy to eliminate the production of the serine protease, Isp-1. We ultimately introduced the spoOA mutation into the triple- and quadruple- protease deficient strains. This feature of our invention is useful only when a promoter, contained within an expression vector for the production of heterologous gene products in a Bacillus host, is not a sporulation-specific promoter (e.g. the spoVG promoter).

Saturating amounts of chromosomal DNA were prepared from *B. subtilis* strain JH646 (spoOA, Prot⁺, Amy⁺, Met⁺) or similar strains having a spoOA mutation, and transformed into competent GP200 cells (Spo⁺, Prot⁻, Amy⁻, Met⁻) Met⁺ transformants were selected by growth on minimal media plates. Resulting transformants were then screened for co-transformation of the spoOA allele by assaying on sporulation medium (Difco) for the sporulation deficiency phenotype, characterised by smooth colony morphology and the lack or, production of a brown pigment. Approximately 9% of the Met⁺ transformants appeared to be co-transformed with the spoOA allele; a number of these were rescreened on plates containing either starch-azure or casein to confirm that the recipients had not also been co-transformed with intact amylase or protease genes from the donor DNA. One transformant that did not exhibit detectable protease activity was designated GP205 (spoOA, amyE, aprA, nprE). Protease levels produced by this host were 0.1% of the level found in the extracellular fluid of the Spo⁺ host, when casein was the substrate.

In the same manner, the spoOA mutation was introduced into the triple protease deficient mutant GP208 (aprΔ, nprΔ, isp-1Δ) and the quadruple protease deficient mutant GP216 (aprΔ, nprΔ, isp-1Δ, eprΔ and described below). The resulting Spo⁻ strains are GP210 and GP235, respectively. These strains are useful when the expression vector is not based on a sporulation dependent promoter.

Identification of a New Protease Gene

We expected that the isolation and cloning of the gene(s) responsible for the remaining protease activity would be difficult using conventional methods because cells did not produce large enough amounts of the enzyme(s) to detect by the appearance of halos on casein plates. We reasoned that it should be possible to isolate the gene(s) if it were replicated on a high-copy vector so that the copy number of the gene(s), and thus protease production, would be amplified to detectable levels. This strategy enabled us to isolate a novel protease gene from a Bacillus gene bank. The first of these new protease genes has been named epr (extracellular protease). Deletion mutants of this new gene were derived in vitro and introduced into the Apr⁻ Npr⁻ Isp⁻ Bacillus host strains by gene replacement methods as described above.

Cloning the epr Gene

Figure 5:
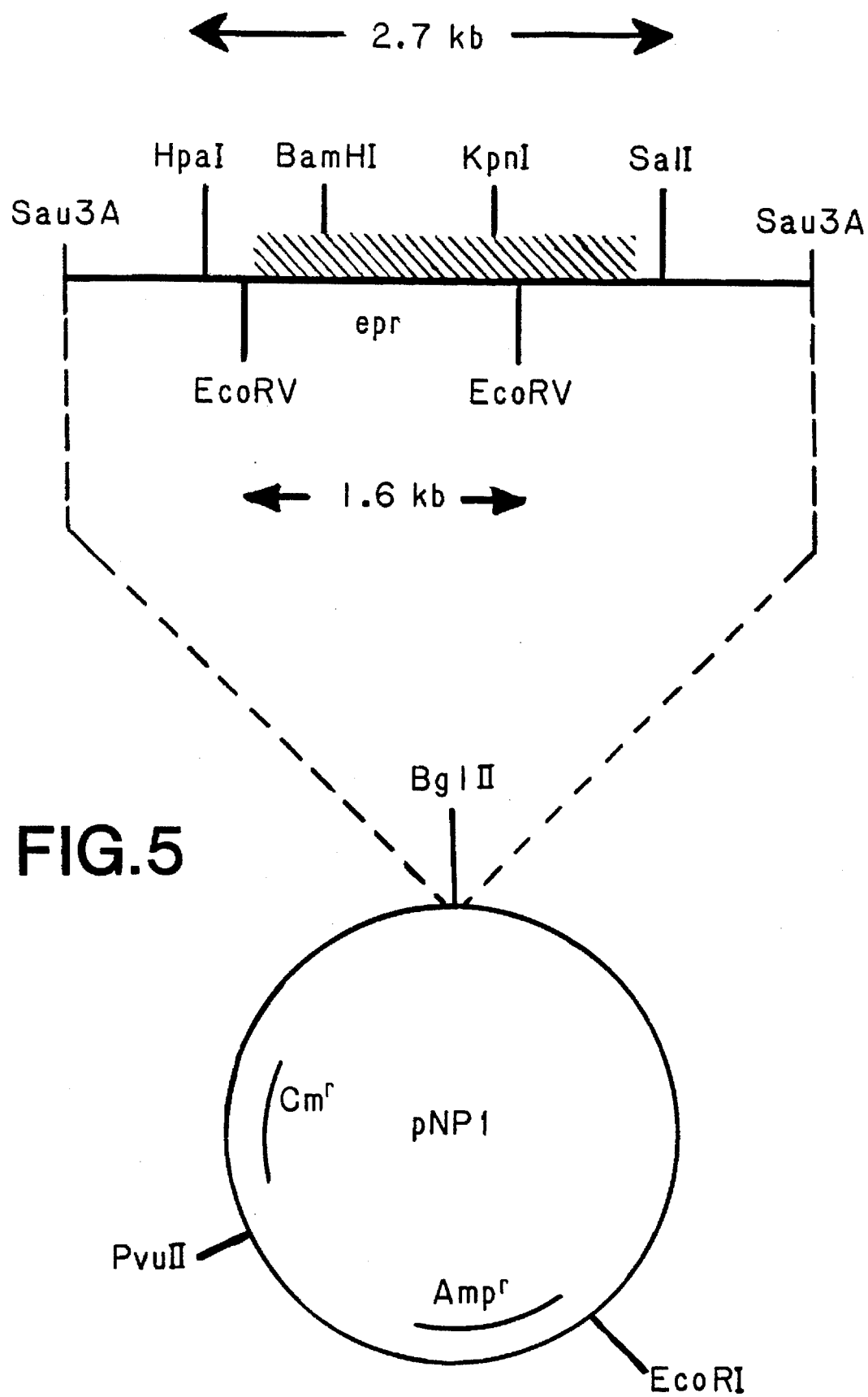
FIG. 5 is a diagrammatic representation of the cloned epr gene, showing restriction enzyme recognition sites.

In order to obtain a clone carrying a gene responsible for residual protease activity, a Sau3A library of *B. subtilis* GP208 DNA was prepared. Chromosomal DNA was isolated, subjected to partial digestion with Sau3A and size-fractionated on an agarose gel. Fragments in the 3–7 kb size range were eluted from the gel and cloned into the BglII site of pEc224 a shuttle vector capable of replicating in both *E. coli* and Bacillus (derived by ligating the large EcoRI-PvuII fragment of pBR322 with the large EcoRI-PvuII fragment of pBD64 (Gryczan et al., 1978, PNAS 75:1428)). The ligated DNA was transformed into *E. coli* JM107 and plated on media containing casein. None of the 1200 *E. coli* colonies produced halos on casein plates, however by restriction analysis of the purified plasmid DNA, approximately 90% of the clones contained inserts with an average size of about 4 kb. The clones were transformed into a Bacillus host to screen for protease activity as follows. *E. coli* transformants were pooled in twelve groups of 100 colonies each (G1–G12). The pooled colonies were grown in liquid media (LB+50 ug/ml ampicillin), plasmid DNA was isolated, transformed into *B. subtilis* GP208 (aprΔ, nprΔ, isp-1Δ) and plated on casein plates. Halos were observed around approximately 5% of transformants from pool G11. Plasmid DNA was isolated from each of the positive colonies and mapped by restriction enzyme digestion. All of the transformants contained an identical insert of approximately 4 kb (FIG. 5). One of these plasmids was selected and named pNP1.

Characterization of epr Protease Activity

The residual protease activity remaining in GP208 (aprΔ, nprΔ, isp-1Δ) cultures accounted for only a small percentage of the total protease activity produced by the host. In order to characterize the type of protease encoded by the epr gene, the effect of different inhibitors on the protease secreted by *B. subtilis* GP208/pNP1 was examined.

Culture media was obtained two hours into stationary phase and assayed using $^{14}$C-casein as the substrate. The level of protease activity present in GP208 was not high enough to detect in the standard protease assay described above, however, appreciable protease activity was detected in the culture medium of GP208/pNP1, carrying the amplified epr gene. The epr protease activity was inhibited in the presence of both 10 mM EDTA and 1 mM PMSF suggesting that it encodes a serine protease which requires the presence of a cation for activity. (Isp-l, another serine protease, is also inhibited by EDTA and PMSF.)

Subcloning the epr Gene

A 2.7 kb HpaI-SalI subfragment was isolated from the pNP1 insert and cloned into pBs81/6, a derivative of pBD64 (derived by changing the PvuII site to a HindIII site using synthetic linkers). Transformants carrying this subcloned fragment were capable of producing halos on casein plates, indicating that the entire protease gene was present within this fragment. A representative clone was named pNP3.

The location of the gene within the pNP3 insert was further defined by subcloning a 1.6 kb EcoRV subfragment into pBs81/6 and selecting for the colonies producing halos on casein plates. A clone which produced a halo, and which also contained the 1.6 kb insert shown in FIG. 5, was designated pNP5. The presence of the protease gene within this fragment was confirmed by deleting this portion of the 4 kb insert from pNP1. pNP1 was digested with EcoRV and religated under conditions which favored recircularization of the vector without incorporation of the 1.6 kb EcoRV insert. The DNA was transformed into GP208 and colonies were screened on casein plates. Greater than 95% of the transformants did not produce halos, indicating that the protease gene had been deleted from these clones. A representative clone was selected and is designated pNP6. (The small percentage of colonies that produced halos were presumed to have vectors carrying the native epr gene resulting from recombination between the chromosomal copy of the gene and homologous sequences within the plasmid.)

Nucleotide and Deduced Amino Acid Sequence of the epr Gene

Subcloning and deletion experiments established that most of the protease gene was contained on the 1.6 kb EcoRV fragment (FIG. 5). Determination of the nucleotide sequence of the 1.6 kb EcoRV fragment (FIG. 6) revealed an open reading frame which covered almost the entire fragment starting 450 bp from the left end and proceeding through the right end (see FIG. 2). Comparison of the deduced amino acid sequence with other amino acid sequences in GENBANK indicated that the protein encoded by the ORF had strong homology (approximately 40%) to both subtilisin (Stahl et al., 1984, J. Bact., 158:411) and Isp-1 (Koide et al., 1986, J. Bact., 167:110) from *B. subtilis* 168. The most probable initiation codon for this protease gene is the ATG at position 1 in FIG. 6. This ATG (second codon in the ORF) is preceded by an excellent consensus *B. subtilis* ribosome binding site (AAAGGAGATGA). In addition, the first 26 amino acids following this methionine resemble a typical *B. subtilis* signal sequence: a short sequence containing two positively-charged amino acids, followed by 15 hydrophobic amino acids, a helix-breaking proline, and a typical Ala X Ala signal peptidase cleavage site (Perlman et al., 1983, J. Mol. Biol., 167:391).

Figure 2:
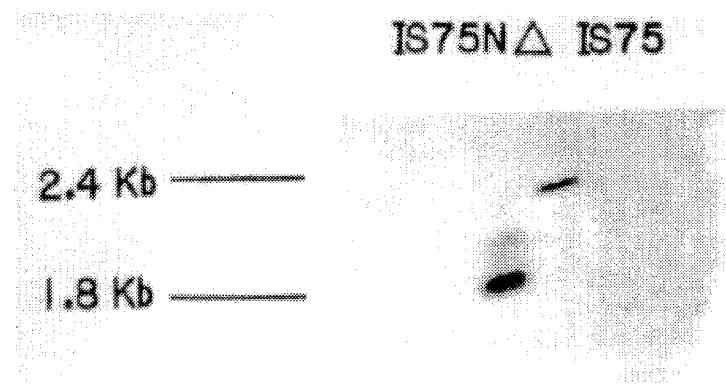
FIG. 2 is a Southern blot of HindIII digested IS75 and IS75NΔ DNA probed with a $^{32}$P-labeled oligonucleotide corresponding to part of the nucleotide sequence of the npr gene.

Sequence analysis indicated that the ORF continued past the end of the downstream EcoRV site, even though the 1.6 kb EcoRV fragment was sufficient to encode Epr protease activity. To map the 3' end of the gene, the DNA sequence of the overlapping KpnI to SalI fragment was determined (FIG. 6). As shown in FIG. 2, the end of the ORF was found 717 bp downstream of the EcoRV site and the entire epr gene was found to encode a 645 amino acid protein, the first approximately 380 amino acids of which are homologous to subtilisin (FIG. 6). The C-terminal approximately 240 amino acids are apparently not essential for proteolytic activity since N-terminal 405 amino acids encoded in the 1.6 kb EcoRV fragment are sufficient for protease activity.

Structure of the epr Protein

In vitro transcription-translation experiments were used to confirm the size of the protein. Plasmid pNP3 DNA (containing the 2.7 kb HpaI-SalI fragment with the entire epr gene) was added to an S30-coupled transcription/translation system (New England Nuclear) resulting in the synthesis of a protein of approximately 75,000 daltons. (Additional proteins of 60,000 and 34,000 daltons were also observed and presumably represented processed or degraded forms of the 75,000 dalton protein.) This size agreed reasonably well with the predicted molecular weight of 69,702 daltons for the primary product based on the deduced amino acid sequence.

The homology between the amino-terminal half of the epr protease and subtilisin suggests that Epr might also be produced as a preproenzyme with a pro sequence of similar size to that of subtilisin (70–80 amino acids). If true, and if there were no additional processing, this would argue that the mature Epr enzyme has a molecular weight of around 58,000. Examination of culture supernatants, however, indicated that the protein has a molecular weight of about 34,000. Comparison by SDS-PAGE of the proteins secreted by *B. subtilis* strain GP208 containing a plasmid with the epr gene (pNP3 or pNP5) or just the parent plasmid alone (pBs81/6) showed that the 2.7 kb HpaI-SalI fragment (FIG. 1) cloned in pNP3 directed the production of proteins of about 34,000 and 38,000 daltons, whereas the 1.6 kb EcoRV fragment cloned in pNP5 in the same orientation (FIG. 1) directed production of just the 34,000 dalton protein. The two proteins appear to be different forms of the Epr protease, resulting from either processing or proteolytic degradation. Clearly, the 1.6 kb EcoRV fragment, which lacks the 3' third of the epr gene, is capable of directing the production of an active protease similar in size to that observed when the entire gene is present. This suggests that the protease normally undergoes C-terminal processing.

Bacillus strain GP208 containing the epr gene on plasmid pNP3 can be used to overproduce the Epr protease, which can then be purified by conventional procedures.

Location of epr on the *B. subtilis* Chromosome

Figure 7:
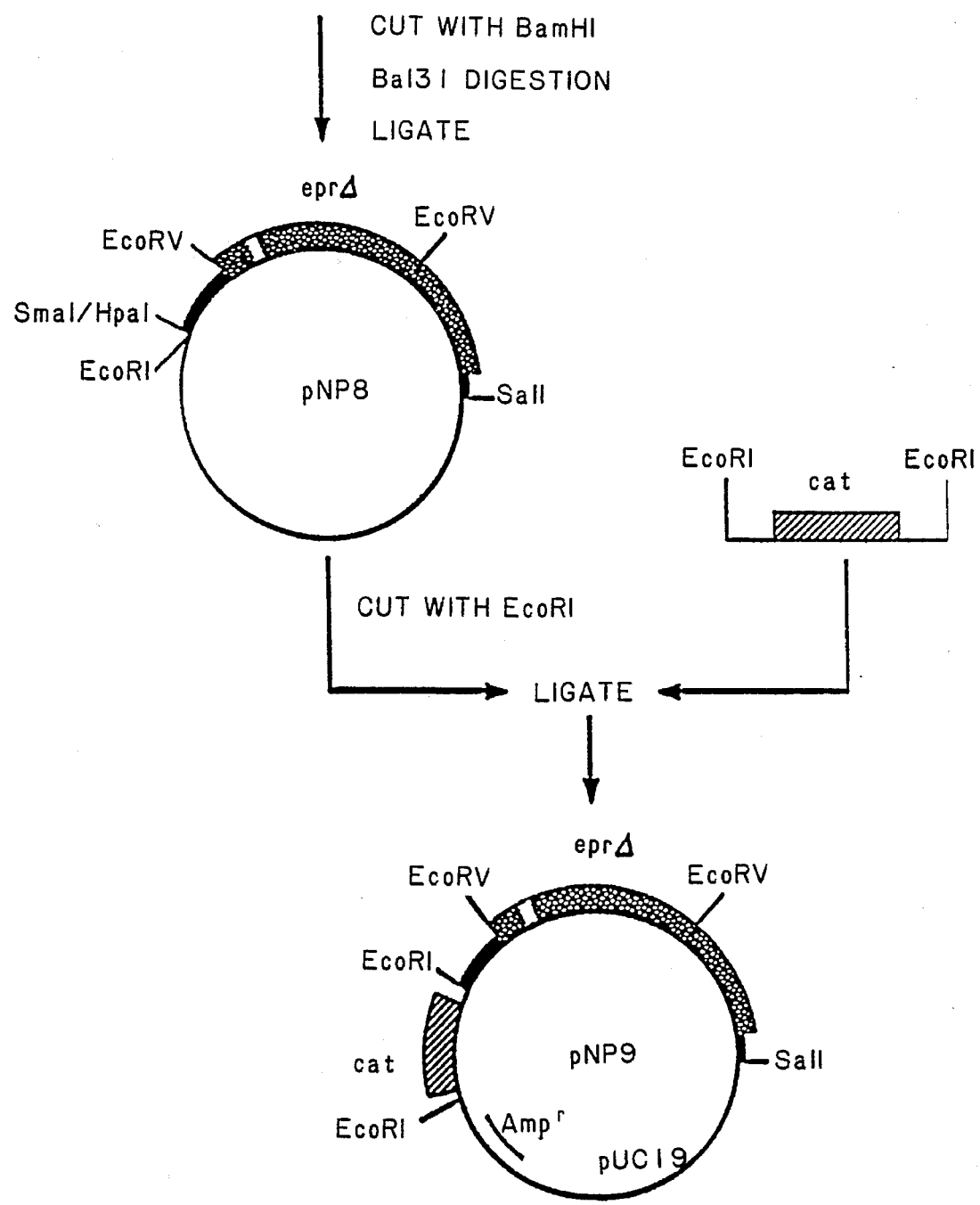
FIG. 7 is a diagrammatic representation of the construction of the plasmid pNP9, which contains the deleted epr gene and the Bacillus cat gene.

To map epr on the *B. subtilis* chromosome, we introduced a drug-resistance marker into the chromosome at the site of the epr gene, and used phage PBS1-mediated transduction to determine the location of the insertion. A 1.3 kb EcoRI fragment containing a chloramphenicol acetyltransferase (cat) gene was cloned into the unique EcoRI site on an *E. coli* plasmid containing the epr gene (pNP2 is depicted in FIG. 7). The resulting plasmid (pNP7) was used to transform *B. subtilis* GP208, and chloramphenicol resistant transformants were selected. Since the plasmid cannot replicate autonomously in *B. subtilis*, the Cm$^r$ transformants were expected to arise by virtue of a single, reciprocal recombination event between the cloned apr gene on the plasmid and the chromosomal copy of the gene. Southern hybridization confirmed that the cat gene had integrated into the chromosome at the site of the cloned epr gene. Mapping experiments indicated that the inserted cat gene and epr gene are tightly linked to sacA321 (77% co-transduction), are weakly linked to purA16 (5% co-transduction), and unlinked to hisA1. These findings suggest that the apr gene is located near sacA in an area of the genetic map which does not contain any other known protease genes.

Construction of Epr Deletion Mutant

To create a mutant Bacillus devoid of protease activity a deletion in the 5' end of the cloned gene was constructed and then used to replace the wild type gene in the chromosome. pNP2 was first digested with BamHI, which cleaves at a unique site within the epr gene, then the linear plasmid DNA was treated with Bal31 exonuclease for 5 minutes at 32° C., religated and transformed into *E. coli* JM107. Plasmid DNA was isolated from 20 transformants, digested with EcoRI and HindIII to remove the epr gene insert and analyzed by gel electrophoresis. One of the plasmids had a 2.3 kb EcoRI-HindIII fragment replacing the 2.7 kb fragment indicating that approximately 400 base pairs had been deleted from the epr gene sequence. This plasmid was designated pNP8 (FIG. 7). This deletion mutant was introduced into *B. subtilis* GP208 by gene replacement methods as described above. The cat gene, contained on an EcoRI fragment from pEccI, was introduced into the EcoRI site on pNP8 to create pNP9 (FIG. 7). This *E. coli* plasmid was used to transform *B. subtilis* GP208 and Cm$^r$ colonies were selected. Most of the transformants produced a very small halo and the remaining 30% produced no halos on casein plates. The absence of a halo and therefore protease activity resulted from a double crossover between chromosomal DNA and homologous sequences from a concatemer of the plasmid DNA; these strains contain the *E. coli* replicon and cat gene flanked by two copies of the deleted epr gene. To screen for a strain that had undergone a recombination event between the two copies of the epr gene to resolve the duplication, but which had jettisoned the cat gene and the *E. coli* replicon, a single colony was selected and grown overnight in rich medium without drug selection. Individual colonies arising from this culture were then screened for drug resistance and about 0.1% of these were found to be Cm$^s$. One such strain GP216, containing deletions within the four protease genes (apr, npr, isp-1 and epr) was selected for further study.

The deletion in the chromosomal epr gene was confirmed by Southern hybridization. GP216, like the Cm$^r$ parent strain, failed to produce a halo on casein plates. In liquid cultures, however, $^{14}$C-casein protease assays indicated that the epr mutation alone does not entirely eliminate residual protease activity. A strain with deletions in epr, apr, npr, and isp, did not produce significantly less protease than a strain with mutations in just apr, npr, and isp. Finally, growth and sporulation of the quadruple protease deleted strain were assayed using standard laboratory media. No differences were observed in growth in LB medium when compared to the wild-type strain. Similarly, no appreciable differences were seen in sporulation frequency after growth on DSM medium for 30 hours ($1 \times 10^8$ spores/ml for both GP208 and GP216).

Identification of Novel Proteolytic Activities

Strains of *B. subtilis* have been deleted for four nonessential protease genes, apr, npr, isp-1 and epr. These deletions reduce total extracellular protease levels in culture supernatants of Spo+ hosts by about 96% compared to the wild-type strain, but it is desirable to decrease or eliminate the remaining 4% residual protease activity for the production of protease-labile products in Bacillus.

Using the azocoll assay, we have identified two novel proteases that account for this residual activity in GP227, a multiple protease deficient *B. subtilis* strain (aprΔ, nprΔ, eprΔ, isp-1Δ) which also contains a gene, sacQ*, encoding a regulatory protein. The sacQ* gene product functions by enhancing the production of degradative enzymes in Bacillus, including the residual protease activity(s) and is the subject of copending application U.S. Ser. No. 921,343, U.S. Pat. No. 5,017,477, assigned to the same assignee and hereby incorporated by reference. Due to enhancement by sacQ*, strain GP227 produces substantially more protease activity than GP216, which lacks sacQ*.

In general, supernatants from cultures of *B. subtilis* GP227 were concentrated, fractionated by passage over a gel filtration column and assayed for protease activity. Two separate peaks of activity were eluted from the column and designated RP-I and RP-II (residual protease) for the larger and smaller molecular weight species, respectively. Subsequent analysis of these two peaks confirmed that each accounted for a distinct enzymatic activity. The isolation and characterization of the RP-I and RP-II proteins, and the creation of a deletion mutation in each of the RP-I and RP-II genes are described below.

Isolation and Characterization of RP-I

A simple and efficient purification scheme was developed for the isolation of RP-I from spent culture fluids.. Cultures were grown in modified MRS lactobacillus media (Difco, with maltose substituted for glucose) and concentrated approximately 10-fold using an Amicon CH2PR system equipped with a S1Y10 spiral cartridge. The concentrated supernatant was dialyzed in place against 50 mM MES, 0.4 M NaCl, pH 6.8, and fractionated over a SW3000 HPLC gel filtration column equilibrated with the same buffer. The fractions containing protease activity were identified using a modification of the azocoll assay described above.

Fractions which were positive for the protease activity, corresponding to the higher molecular weight species, were pooled and concentrated using a stirred cell equipped with a YM5 membrane, dialyzed vs. 50 mM MES, 100 mM KCl, pH 6.7 and applied to a benzamidine-Sepharose liquid affinity column equilibrated with the same buffer. Most of the protein applied to the column (97%) failed to bind to the resin, however RP-I protein bound quantitatively and was eluted from the column with 250 mM KCl.

SDS-PAGE analysis of the benzamidine purified RP-I revealed that the protein was greater than 95% homogeneous, and had a molecular weight of approximately 47,000 daltons. Purification by the above outlined procedure resulted in a 140-fold increase in specific activity, and an overall recovery of about 10%.

Isoelectric focusing gels revealed that RP-I has a pI between 4.4 and 4.7, indicating a high acidic/basic residue composition. The enzyme has a pH optimum of 8.0 and a temperature maximum of 60° C. when azocoll is used as the substrate. It is completely inhibited by PMSF, indicating that it is a serine protease, but it is not inhibited by EDTA, even at concentrations as high as 50 mM.

RP-I catalyzes the hydrolysis of protein substrates such as denatured collagen and casein, as well as ester substrates (O=C—O— vs. O=C—N— linkages) such as N-α-benzolyl-L-arginine ethyl ester, phenylalanine methylester, tyrosine ethyl ester and phenylalanine ethyl ester, but does not catalyze hydrolysis of the arginine peptide bond in the synthetic substrate N-α-benzoyl-L-arginine-4-nitranilide. Collectively, these data demonstrate that RP-I is a serine endoproteinase that has esterase activity and belongs to the subtilisin superfamily of serine proteases. Furthermore, these characteristics indicate that RP-I may be the enzyme commonly referred to as Bacillopeptidase F (Boyer et al., 1968, Arch Biochem, Biophys., 128:442 and Roitsch et al., 1983, J. Bact., 155:145). Although Bacillopeptidase F has been reported to be a glycoprotein, we have not found carbohydrate to be associated with RP-I.

Cloning the Gene for RP-I

The sequence of the amino-terminal 28 amino acids of RP-I was determined by sequential Edman degradation on an automatic gas phase sequenator and is depicted in FIG. 8. A DNA probe sequence (81 nucleotides) was synthesized based on the most frequent codon usage for these amino acids in *B. subtilis* (FIG. 8). The N-terminal amino acid sequence of RP-I contains two tryptophan residues (positions 7 and 18). Since tryptophan has no codon degeneracy, this facilitated the construction of a probe that was highly specific for the gene encoding RP-I.

High molecular weight DNA was isolated from *B. subtilis* strain GP216, digested with each of several different restriction endonucleases and fragments were separated by electrophoresis through a 0.8% agarose gel. The gel was blotted onto a nitrocellulose filter by the method of Southern (supra) and hybridized overnight with the $^{32}$P end-labeled synthetic RP-I specific probe under semi-stringent conditions (5× SSC, 20% formamide, 1× Denhardts at 37° C.). Following hybridization, the blot was washed for one hour at room temperature in 2× SSC, 0.1% SDS.

The RP-I specific probe hybridized to only one band in each of the restriction digests indicating that the probe was specific for the RP-I gene. In the PstI digest, the probe hybridized to a 6.5 kb fragment which was a convenient size for cloning and was also large enough to contain most or all of the RP-I gene.

A clone bank containing PstI inserts in the 6–7 kb size range was prepared from *B. subtilis* DNA as follows. Chromosomal DNA of strain GP216 was digested with PstI and separated on a 0.8% agarose gel. DNA fragments of 6–7 kb were purified from the gel by electroelution and ligated with PstI digested pBR322 that had been treated with calf intestinal phosphatase to prevent recircularization of the vector upon treatment with ligase. The ligated DNA was transformed into competent *E. coli* DH5 cells and plated on media containing tetracycline. Approximately $3\times10^4$ Tet$^r$- transformants resulted, 80% of which contained plasmids with inserts in the 6–7 kb size range.

A set of 550 transformants was screened for the presence of the RP-I insert by colony hybridization with the $^{32}$P-labeled RP-I specific probe and seven of these transformants were found to hybridize strongly with the probe. Plasmid DNA was isolated from six of the positive clones and the restriction digest patterns were analyzed with PstI and HindIII. All six clones had identical restriction patterns, and the plasmid from one of them was designated pCR83.

Figure 9:
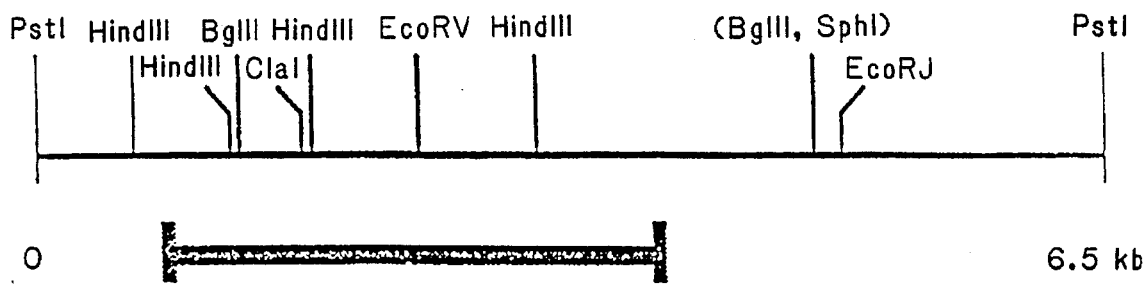
FIG. 9 is a restriction map of the 6.5 kb insert of plasmid pCR83, which encodes the RP-I protein.

Using a variety of restriction enzymes, the restriction map of pCR83 insert shown in FIG. 9 was derived. The RP-I oligomer probe, which encodes the N-terminal 28 amino acids of the mature RP-I protease, was hybridized with restriction digests of pCR83 by the method of Southern (supra). The probe was found to hybridize with a 0.65 kb ClaI-EcoRV fragment suggesting that this fragment contained the 5' end of the gene. In order to determine the orientation of the RP-I gene, the strands of the ClaI-EcoRV fragment were separately cloned into the single-stranded phage M13. The M13 clones were then probed with the RP-I oligomer and the results indicated that the RP-I gene is oriented in the leftward to rightward direction according to the map in FIG. 9.

The DNA sequence of a portion of the PstI insert, as shown in FIG. 9, was determined, and an 81 base pair sequence (underlined in FIG. 10) was found that corresponded exactly with the sequence encoding the first 28 amino acids of the protein. The BglII and ClaI sites designated in FIG. 10 are identical to those designated in FIG. 9 and, in addition, the EcoRV site is identical to that designated in the restriction enzyme map shown in FIG. 9. Portions of the untranslated region surrounding the RP-I coding region are also shown in FIG. 10; the DNA sequence underlined within the 5' untranslated region corresponds to the putative ribosome binding site.

The DNA sequence revealed an open reading frame that began at position-15 (in FIG. 10) and proceeded through to position 2270. The most probable initiation codon for this open reading frame is the ATG at position 1 in FIG. 10. This ATG is preceded by a ribosome binding site (AAAGGGG-GATGA), which had a calculated of −17.4 kcal. The first 29 amino acids following this Met resemble a *B. subtilis* signal sequence, with a short sequence containing five positively-charged amino acids, followed by 16 hydrophobic residues, a helix-breaking proline, and a typical Ala—X—Ala signal peptidase cleavage site. After the likely signal peptidase cleavage site, a "pro" region of 164 residues is followed by the beginning of the mature protein as confirmed by the determined N-terminal amino acid sequence. The first amino acid of the N-terminus, which was uncertain from the protein sequence, was confirmed as the Ala residue at position 583–585 from the DNA sequence. The entire mature protein was deduced to contain 496 amino acids with a predicted molecular weight of 52,729 daltons. This size was in reasonable agreement with the determined molecular weight of the purified protein of 47,000 daltons. In addition, the predicted isoelectric point of the mature enzyme (4.04) was in good agreement with the observed pI of 4.4–4.7. GENBANK revealed that the RP-I gene is partially homologous (30%) to subtilisin, to ISP-l and, to a lesser extent (27%), to the epr gene product.

Cloning the RP-I Gene on a Multicopy Replicon

The PstI fragment was removed from pCR83 and ligated into PstI linearized pBD9, a multicopy Bacillus replicon encoding erythromycin and kanamycin resistances. The ligated DNA was transformed into competent GP227 cells (the sacQ* enhancement strain) and kanamycin resistant transformants were selected. A plasmid carrying the 6.5 kb PstI insert was chosen and designated pCR88.

To confirm that this insert encoded the RP-I gene, GP227 cells containing pCR88 or pBD9 were grown in MRS medium under selective conditions for 50 hours at 37° C. Supernatant samples were collected and assayed for protease activity. Supernatants from the pCR88 cultures contained approximately 10-fold more protease activity than those from the pBD9 cultures. Furthermore, this secreted protease activity was inhibited by PMSF and, when fractionated on a denaturing protein gel, the supernatant from the pCR88 sample contained an extra protein of 47 kd. These results confirmed that the RP-I gene was encoded within the 6.5 kb fragment, and that cloning the sequence in a multicopy replicon leads to the overproduction of the RP-I protein.

Location of the RP-I Gene on the *B. Subtilis* Chromosome

We mapped the location of the RP-I gene (bpr) on the *B. subtilis* chromosome by integrating a drug resistance marker into the chromosome at the site of bpr and using phage PBS1-mediated transduction to determine the location of the cat insertion. A 1.3 kb SmaI fragment containing a chloramphenicol acetyltransferase (cat) gene was cloned into the unique EcoRV site of pCR92 (the 3.0 kb BglII of pCR83 cloned into pUC18. The EcoRV site is in the coding region of bpr (FIG. 10). The resulting plasmid, pAS112, was linearized by digestion with EcoR1 and then used to transform *B. subtilis* strain GP216, and chloramphenicol-resistant transformants were selected (GP238). $Cm^r$ transformants were expected to be the result of a double cross-over between the linear plasmid and the chromosome (marker replacement). Southern hybridization was used to confirm that the cat gene had integrated in the chromosome, interrupting the bpr gene. Mapping experiments indicating that the inserted cat gene and bpr were strongly linked to pyrD1 (89%) and weakly linked to metC (4%). The gene encoding the neutral protease gene (npr) also maps in this region of the chromosome, although npr is less tightly linked to pyr (45% and 32%) and more tightly linked to metC (18% and 21%) than is bpr.

Construction of a Deleted Version of the RP-I Gene

An internal deletion in the RP-I sequence was generated in vitro. Deletion of the 650 bp sequence between the ClaI and EcoRV sites in the pCR83 insert removed the sequence encoding virtually the entire amino-terminal half of the mature RP-I protein. The deletion was made by the following procedure.

The 4.5 kb PstI-EcoRI fragment of pCR78 (a pBR322 clone containing the 6.5 kb PstI fragment) was isolated and ligated to pUC18 (a vector containing the *E. coli* lacZ gene encoding β-galactosidase) that had been digested with EcoRI and PstI. The ligation mix was then transformed into *E. coli* DH5 cells. When plated onto LB media containing Xgal and ampicillin, eight white colonies resulted, indicating insertion of the fragment within the gene encoding β-galactosidase. Plasmid DNA prepared from these colonies indicated that seven of the eight colonies contained plasmids with the 4.5 kb insert. One such plasmid, pKT2, was digested with EcoRV and ClaI, treated with Klenow fragment to blunt the ClaI end and then recircularized by self-ligation. The ligated DNA was then transformed into *E. coli* DH5 cells, Approximately 100 transformants resulted and plasmid DNA was isolated from $Amp^r$ transformants and analyzed by restriction digestion. Eight of eight clones had the ClaI-EcoRV fragment deleted. One such plasmid was designated pKT2'. The cat gene, carried on an EcoRI fragment from pEccI was then ligated into pKT2' for use in selecting Bacillus integrants as described above. To insert the cat gene, pKT2' was digested with EcoRI, treated with calf intestine alkaline phosphatase and ligated to a 1.3 kb EcoRI fragment containing the cat gene. The ligated DNA was transformed into DH5 cells and the $Amp^r$ colonies that resulted were patched onto LB media containing chloramphenicol. Two of 100 colonies were $Cm^r$. Plasmid DNA was isolated from these two clones and the presence of the 1.3 kb cat gene fragment was confirmed by restriction enzyme analysis of plasmid DNA. One of these plasmids, pKT3, was used to introduce the deleted gene into strain GP216 by gene replacement methods.

The DNA was transformed into GP216 and chloramphenicol resistant colonies were selected. Chromosomal DNA was extracted from 8 $Cm^R$ colonies and analyzed by Southern hybridization. One clone contained two copies of the deleted RP-I gene resulting from a double crossover between homologous sequences on the vector and in the chromosome. The clone was grown in the absence of chloramphenicol selection and was then replica plated onto TBAB media containing chloramphenicol. One $Cm^s$ colony was isolated and Southern analysis confirmed that the deleted gene had replaced the wild-type RP-I gene in the chromosome. This strain was designated GP240. Analysis of supernatants from cultures of GP240 confirmed the absence of RP-I activity.

Isolation and Characterization of RP-II

The purification scheme for RP-II was more extensive than for RP-I because RP-II failed to bind benzamidine-Sepharose or other protease-affinity resins, e.g., arginine-Sepharose and hemoglobin-agarose, and we thus found it necessary to use more conventional purification techniques such as ion exchange chromatography, gel filtration and polyacrylamide gel electrophoresis.

Concentrated crude supernatants of GP227 cultures were fractionated over DEAE-Sephacel (anion exchange) equilibrated at pH 6.8. At this pH the RP-II protein failed to bind the resin; however, approximately 80% of the total applied protein, including RP-I, bound the resin and was thus removed from the sample. The column eluate was then fractionated by cation exchange chromatography using CM-Sepharose CL-6B equilibrated at pH 6.8. RP-II was capable of binding to the resin under these conditions and was then eluted from the column with 0.5 M KCl. To further enhance the resolution of the cation exchange step, the RP-II eluate was then refractionated over a 4.6×250 mm WCX (weak cation exchange) HPLC column developed with a linear gradient of NaCl. The WCX pool was then size-fractionated over a TSK-125 HPLC column. The RP-II peak was then fractionated a second time over the same column yielding a nearly homogeneous preparation of RP-II when analyzed by SDS-PAGE. The protease, was purified over 6900-fold and represented approximately 0.01% of the total protein in culture fluids of GP227. Alternatively, approximately 30 fold more RP-II can be purified from a Bacillus strain that is RP-I⁻ and contains the sacQ* enhancing sequence (U.S. Ser. No. 921,343, assigned to the same assignee and hereby incorporated by reference), since the quantity of RP-II produced by such a strain is substantially increased, representing about 0.3% of total protein in the culture fluid.

RP-II was insensitive to PMSF treatment, and therefore is not a serine protease. SDS-PAGE analysis indicated that RP-II has a molecular mass of 27.3 kd. The failure of RP-II to bind DEAE at pH 6.7 and PAE-300 (an HPLC anionic column) at pH 8.3 indicated that the protein has a basic isoelectric point which is greater than 8.3 (pI=8.7 by chromatofocusing). RP-II is highly sensitive to dithiothreitol (DTT, a sulfhydryl reducing agent), being quantitatively inhibited at levels as low as 1 mM in the azocoll assay. RP-II is also sensitive to combinations of other sulfhydryl reagents with metal chelators (i.e., mercaptoethanol with EDTA). Inhibition of proteases by sulfhydryl reagents is relatively rare and has only been described for a few proteases, such as collagenase from *C. histolyticum* and carboxypeptidase A. RP-II also possesses esterase activity as demonstrated by its ability to hydrolyze phenylalanine methyl ester and n-t-BOC-L-glutamic acid-α-phenyl ester.

In order to obtain the cleanest possible sample of RP-II for sequence analysis, a final purification step was used which involved separation by polyacrylamide gel electrophoresis. Following electrophoresis, proteins were transferred electrophoretically from the gel to a sheet of polyvinylidene difluoride (PVDF) membrane. RP-II was visualized on the hydrophobic membrane as a "wet-spot" and the corresponding area was cut from the sheet and its amino-terminal amino acid sequence determined.

The sequence of the 15 amino acid terminal residues of RP-II (Ser—Ile—Ile—Gly—Thr—Asp—Glu—Arg—Thr—Arg—Ile—Ser—Ser—Thr—Thr—) is rich in serine and arginine residues. Since both serine and arginine have a high degree of codon degeneracy, this increased the difficulty in creating a highly specific probe. Therefore, additional amino acid sequence information was obtained from internal peptides that contained one or more non-degenerate amino acid residues.

Sequence Analysis of Internal Peptide Fragments of RP-II

Tryptic peptides from purified RP-II were produced and isolated using reverse-phase HPLC. Since each of the amino acids tryptophan and methionine is encoded by only one amino acid codon, a synthetic nucleotide probe, or "guess-mer" that encodes one or more of either of these amino acids will be highly specific for its complementary nucleotide sequences.

An HPLC chromatogram of the RP-II trypsin digested mixture was monitored at three wavelengths: 210 nm (peptide bonds), 227 nm (aromatic residues, i.e., phenylalanine, tyrosine, tryptophan), and 292 nm (conjugated ring structure of tryptophan). The 292 nm trace was used to identify peptides of RP-II that contain a tryptophan residue. The 210 nm trace was used to obtain baseline resolved (i.e., single-species peptides) fragments for sequence analysis. Based on the 210 nm and 292 nm traces, three fragments were chosen for sequence analysis: T90, T94, and T92. Guess-mer oligomers were then synthesized based on the amino acid sequences of these fragments.

FIG. 11(*a*) is the amino-terminal sequence obtained for RP-II fragment T90. A total of 15 residues were obtained, 67% of which have only one or two possible codons. The specificity of a probe (BRT90) constructed based on the sequence of fragment T90 was enhanced by the presence of a predicted tryptophan residue (position 12). The number in parentheses at each position represents the possible number of codons for each residue.

The amino-terminal sequence of RP-II fragment T94 is shown in FIG. 11(*b*). Of the 30 residues determined, none were found to be tryptophan. Although only 36% of the residues (numbers 1–25) have two possible codons, the length of the corresponding 75-met probe (707) renders it useful for corroborating hybridization experiments conducted with the T90 probe.

The third and final probe was constructed based on sequence information obtained from RP-II fragment T92 (FIG. 11(*c*)). Because of the relatively high degree of degeneracy at the beginning and end of this sequence, a probe was constructed based on residues 15–27. The resulting 39-mer probe (715) codes for a peptide of which half the residues have only one or two possible codons. Furthermore, the specificity of this probe was enhanced by the tandem location of a methionine and tryptophan residue at positions 26 and 27.

Cloning of RP-II

Chromosomal DNA was cut with various restriction enzymes and a series of hybridizations using the radiolabelled oligomer probes BRT90 and 707 were performed. Both probes were labelled with $^{32}P$ and hybridized to a Southern blot of GP241 DNA digested with BamHI, BglII, HincII, PstI, or EcoRI under semi-stringent conditions (5× SSC, 10% formamide, 1× Denhardt's, 100 µg/ml denatured salmon sperm DNA at 37° C.). After hybridization for 18 hours, the blots were washed with 2× SSC, 0.1% SDS for one hour at 37° C., and then washed with the same buffer at 45° C. for one hour. The results are shown in FIG. 12. Both probes hybridized to the same restriction fragments: HincII, ~1 kb; PstI, 3–4 kb; and EcoRI, 6–7 kb. The probes also hybridized to very large fragments in the BamHI and BglII-digested DNAs.

PstI fragments of 3–4 kb were used to construct a DNA library, as follows. pBR322 was digested with PstI and treated with CIAP. Size-selected PstI-digested GP241 chromosomal DNA of 3–4.5 kb was electroeluted from a 0.8% agarose gel. Approximately 0.1 µg of PstI-cut pBR322 and 0.2 µg of the size-selected DNA was ligated at 16° C. overnight. The ligated DNA was then transformed into *E. coli* DH5 cells. Approximately 10,000 colonies resulted, of which 60% contained plasmids with the insert DNA. 1400 colonies were patched onto LB plates containing 15 µg/ml tetracycline with nitrocellulose filters. After colonies were grown at 37° C. overnight, the filters were processed to lyse the colonies, denature the DNA, and remove cell debris. The filters were then baked at 80° for two hours. Colony hybridization was performed using radiolabelled probe 707. Hybridization conditions were identical to those used in the Southern blot experiments. Analysis of the plasmid DNA from four positive colonies identified one as containing plasmid DNA that contained a 3.6 kb insert which strongly hybridized to both probes. The plasmid, pLP1, is shown in FIG. 13(*b*).

A restriction map of pLP1 (FIG. 13(*a*)) was constructed using a variety of restriction endonucleases to digest pLP1, transferring the size-fractionated digests onto nitrocellulose, and probing the immobilized restriction fragments with the radiolabelled oligomers described above. It was determined that all three oligomers, which encode a total of 53 amino acids within the RP-II protein, hybridized with the 1.1 kb HincII fragment.

The 1.1 kb HincII fragment was isolated and cloned into M13mp18. A phage clone containing the HincII fragment was identified by hybridization with one of the oligomer probes. The DNA sequence of the HincII fragment revealed an open reading frame that spanned most of the fragment (position −24 to position 939 in. FIG. 14). The most probable initiation codon for this open reading frame is the ATG at position 1 in FIG. 14. This ATG is preceded by a *B. subtilis* ribosome binding site (AAAGGAGG), which has a calculated ΔG of −16.0 kcal. The first 33 amino acids following this Met resembled a *B. subtilis* signal sequence, with a short sequence containing four positively-charged amino acids, followed by 18 hydrophobic residues, a helix-breaking proline, and a typical Ala—X—Ala signal peptidase cleavage site. After the presumed signal peptidase cleavage site, a "pro" region of 58 residues is found, followed by the beginning of the mature protein as determined by the N-terminal amino acid sequence of the purified protein.. The amino terminal 16 residues are underlined and designated "N-terminus". Amino acid sequences from which the three guess-mers were deduced are also underlined and designated T94, T92, and T90. The determined amino acid sequences of the peptides matched the deduced amino acid sequence except for a serine residue encoded by nucleotides 379–381 and a cysteine residue encoded by nucleotides 391–393. The determined amino acid sequence predicted a cysteine residue (position 14, T94 peptide) and an asparagine residue (position 18, T94 peptide), respectively (FIG. 11). The entire mature protein was deduced to contain 221 amino acids with a predicted molecular weight of 23,941 daltons. This size was in approximate agreement with the determined molecular weight of the purified protein 28,000 daltons.

The deduced amino acid sequence showed only limited homology to other sequences in GENBANK. The strongest homology was to human protease E and bovine procarboxypeptidase A in a 25 amino acid sequence within RP-II (131–155, encoded by nucleotides 391–465; FIG. 14).

To further confirm the identity of the RP-II gene, the 3.6 kb PstI fragment was engineered onto a multi-copy Bacillus replicon to test for overproduction of the RP-II protein. For this purpose the Bacillus plasmid pBs81/6 (Cm$^r$, Neo$^r$) was inserted into the E. coli clone containing the RP-II gene. Plasmid pLP1 (8.0 kb) was digested with EcoRI, which cuts at a single site outside the PstI insert, and ligated to EcoRI-digested pBs81/6 (4.5 kb; FIG. 13(a)). The resulting plasmid (pCR130) was used to transform GP241, and chloramphenicol or neomycin-resistant transformants were selected. Supernatant samples from cultures of the transformants were found to contain 3–4 fold more azocoll-hydrolyzing activity than the supernatants from cells containing only the plasmid pBs81/6, indicating that the gene for RP-II is wholly contained within the 3.6 kb PstI fragment.

Location of the RP-II Gene on the B. subtilis Chromosome

In order to map the RPII gene (mpr) on the B. subtilis chromosome, we used B. subtilis strain GP261 described below which contained the cat gene inserted into the chromosome at the site of the mpr gene and used phage PBS1 transduction to determine the location of the cat insertion.

Mapping experiments indicated that the inserted cat gene and mpr were linked to cysA14 (7% co-transduction) and to aroI906 (36% co-transduction) but unlinked to purA16 and dal. This data indicated that the mpr gene was between cysA and aroI in an area of the genetic map not previously known to contain protease genes.

Deletion of the RP-II Gene on the Bacillus Chromosome

As described above for the other Bacillus subtilis proteases, an RP-II Bacillus deletion mutant was constructed by substituting a deleted version of the RP-II gene for the complete copy on the chromosome. To ensure the deletion of the entire RP-II gene, a region of DNA was deleted between the two HpaI sites in the insert (FIG. 13(a)). This region contains the entire 1.1 kb HincII fragment and an additional 0.9 kb of DNA upstream of the HincII fragment.

To create the deletion, plasmid pLP1 (the pBR322 clone containing the 3.6 kb PstI fragment) was digested with HpaI and size-fractionated on an agarose gel. Digestion of pLP1 results in the release of the 2 kb internal HpaI fragment and a larger HpaI fragment containing the vector backbone and segments that flank the PstI insert (FIG. 13(c)). The larger HpaI fragment was purified and ligated with purified blunt-ended DNA fragments containing either the chloramphenicol-resistance (cat) gene from pMI1101 (Youngman et al., 1984, supra) or the bleomycin resistance (ble) gene from pKT4, a derivative of pUB110 (available from the Bacillus Stock Center, Columbus Ohio).

The cat gene was isolated as a 1.6 kb SmaI fragment from pEccl. This DNA was ligated to the isolated large HpaI fragment of pLP1. The ligated DNA was then transformed into E. coli DH5 cells. Approximately 20 Tet$^r$ colonies resulted. One colony was found to be Cm$^r$ when the colonies were patched onto LB medium +5 μg/ml chloramphenicol. Analysis of the plasmid DNA from this colony confirmed the presence of the cat gene. This plasmid was called pLP2.

Plasmid pLP2 (FIG. 13(c)) was digested with PstI and then transformed into GP241. This transformation gave approximately 280 Cm$^r$ colonies; one colony was chosen for further study (GP261). Competent cells of GP261 were prepared and then transformed with pDP104 (sacQ*): 10 Tet$^r$ colonies resulted. Four colonies were grown in MRS medium and the presence of sacQ* was confirmed by elevated levels of aminopeptidase. This strain was called GP262.

Since the cat gene was often used to select other vectors, a different antibiotic resistance was also used to mark the deletion of the RP-II gene on the Bacillus chromosome; i.e., the bleomycin-resistance gene of pUB110. The ble gene was isolated from plasmid pKT4, a derivative of pUB110, as an EcoRV-SmaI fragment and ligated to the purified large HpaI fragment (FIG. 13(c)) before tranformation into E. coli DH5 cells; tetracycline-resistant transformants were selected and then screened for resistance to phleomycin, a derivative of bleomycin, by patching onto TBAB plates containing phleomycin at a final concentration of 2 μg/ml. Of 47 Tet$^r$ transformants so screened, seven were also phleomycin-resistant. The insertion of the ble gene was confirmed by restriction analysis of the plasmids isolated from these clones. One of these plasmids, pCR125 (FIG. 13(c)), was used to introduce the deleted gene containing the ble gene marker into the strain GP241 by gene replacement methods, as described below.

Plasmid pCR125 was digested with EcoRI and the linear plasmid DNA was used to transform GP241 to phleomycin resistance. Resistant transformants were selected by plating the transformed cells onto TBAB agar plates containing a gradient of 0–5 μg/ml phleomycin across the plate. Transformants that were resistant to approximately 2.5 μg/ml phleomycin on the plates were single-colony purified on TBAB phleomycin plates and thereafter grown on TBAB without selective antibiotic (strain GP263).

The strains bearing the RP-II deletion and the cat or ble insertion in the RP-II gene, along with the positive regulatory element, sacQ*, were evaluated for extracellular enzyme production, particularly protease and esterase activities.

The data given in Table 1, below, indicate that the presence of sacQ* in B. subtilis strain GP239, which bears null mutations in the five protease genes apr (subtilisin), npr (neutral protease), epr (extracellular protease), isp (internal serine protease), and bpr enhanced production of the RP-II protease (which also has esterase activity). To assess the influence on protease production of deleting RP-II from strains of *B. subtilis* bearing the sacQ* regulatory element, the following experiments were performed.

Independent clones of the RP-II deletion strain GP262 were shown to produce negligible amounts of esterase activity and no detectable levels of endoprotease activity using azocoll as substrate (Table I). To confirm the absence of protease activity, culture supernatants from GP262 were concentrated to the extent that the equivalent of 1 ml of supernatant could be assayed. Even after 2.5 hours incubation of the equivalent of 1 ml of supernatant with the azocoll substrate, there was no detectable protease activity in the deleted RP-II strain. By comparison, 50 µl of supernatant from GP239 typically gave an $A_{520}$ in the azocoll assay of over 2.0 after a one hour incubation at 55° C. (The presence of sacQ* was confirmed by measurement of the levels of aminopeptidase present in the culture fluids of this strain, which were 50–80 fold higher than in analogous strains lacking sacQ*.) Thus, deletion of the two residual proteases, RP-I and RP-II, in Bacillus yields a strain that is largely incapable of producing extracellular endoproteases, as measured using azocoll as a substrate under the conditions described above.

TABLE 1

| Strain | Aminopeptidase (U/ml) | Protease (U/ml) | Esterase (U/ml) |
| --- | --- | --- | --- |
| GP238 | 0.04 | 0.13 | 0.02 |
| GP239 | 1.7 | 84 | 1.16 |
| GP262, AI | 2.9 | ND | 0.08 |
| GP262, AII | 3.4 | ND | 0.11 |
| GP262, BI | 1.9 | ND | 0.10 |
| GP262, BII | 2.5 | ND | 0.10 |

Aminopeptidase was measured using L-leucine-p-nitroanilide as substrate (1 unit=µmols substrate hydrolyzed/minute). Protease was measured using the standard azocoll assay (1 unit=$\Delta A_{520}$ of 0.5/hour). Esterase was measured using N-t-BOC-glutamic acid-α-phenyl ester as substrate (1 unit=µmols substrate hydrolyzed/minute). Strain GP238 has the genotype Δapr, Δnpr, Δepr, Δisp, Δrp-1; strain GP239 has the genotype Δapr, Δnpr, Δepr, Δisp, Δrp-1, sacQ*; and GP262 AI, AII, BI, and BII are independent clones of GP262 containing sacQ* and a cat insertional deletion in RP-II. ND means not detectable.

Referring to Table 2, several protease-deficient strains were also tested for protease activity using the more sensitive resorufin-labelled casein assay described earlier. As is shown in Table 2, although the strain GP263, deleted for six protease genes, exhibited no detectable protease activity in the azocoll test, such activity was detected in the resorufin-labelled casein test. GP271, the spoOA derivative of GP263, exhibited no detectable protease activity in either test, indicating that the prior protease activity detected in GP263 may be under sporulation control. The minor casein-detectable activity present in culture fluids of GP263 apparently belongs to the serine protease family, because of its sensitivity to inhibition by PMSF. In the presence of PMSF, no detectable protease activity was present in cultures of GP263.

TABLE 2

| Strain | Genotype | Remaining activity (% of wild-type at $t_{20}$) | |
| --- | --- | --- | --- |
| | | 1 | 2 |
| IS75 | Wild-type | 100 | 100 |
| GP202 | Δapr, Δnpr, amyE | 5 | 8 |
| GP208 | Δapr, Δnpr, Δisp-1, amyE, met⁻ | 5 | 8 |
| GP263 | Δapr, Δnpr, Δisp-1, Δepr, Δbpr, Δmpr, Δhpr, amyE, met⁻ | ND | 0.5–1 |
| GP271 | spoOA, Δapr, Δnpr, Δisp-1, Δepr, Δbpr, Δmpr, Δhpr, amyE, met⁻ | ND | ND |

1 As measured using azocoll as substrate.
2 As measured using resorufin casein as substrate.

Other Embodiments

Other embodiments are within the following claims. For example, in some instances it may be desirable to express, rather than mutate or delete, a gene or genes encoding protease(s) of the invention. This could be done, for example, to produce the proteases for purposes such as improvement of the cleaning activity of laundry detergents or for use in industrial processes. This can be accomplished either by inserting regulatory DNA (any appropriate Bacillus promoter and, if desired, ribosome binding site and/or signal encoding sequence) upstream of the protease-encoding gene or, alternatively, by inserting the protease-encoding gene into a Bacillus expression or secretion vector; the vector can then be transformed into a Bacillus strain for production (or secretion) of the protease, which is then isolated by conventional techniques. Alternatively, the protease can be overproduced by inserting one or more copies of the protease gene on a vector into a host strain containing a regulatory gene such as sacQ*.

We claim:

1. An isolated and purified DNA molecule encoding a Bacillus residual protease I (bpr).
2. A vector comprising a Bacillus gene encoding RP-I and regulator DNA operably linked to said gene.
3. A Bacillus cell transformed with the vector of claim 2.

\* \* \* \* \*